US010292610B2

(12) United States Patent
Srivastava

(10) Patent No.: US 10,292,610 B2
(45) Date of Patent: *May 21, 2019

(54) NEUROMODULATION SYSTEMS HAVING NERVE MONITORING ASSEMBLIES AND ASSOCIATED DEVICES, SYSTEMS, AND METHODS

(71) Applicant: Medtronic Ardian Luxembourg S.a.r.l., Luxembourg (LU)

(72) Inventor: Nishant R. Srivastava, Sunnyvale, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 367 days.

This patent is subject to a terminal disclaimer.

(21) Appl. No.: 15/087,798

(22) Filed: Mar. 31, 2016

(65) Prior Publication Data

US 2016/0287114 A1    Oct. 6, 2016

Related U.S. Application Data

(63) Continuation of application No. 14/015,793, filed on Aug. 30, 2013, now Pat. No. 9,326,816.

(51) Int. Cl.
*A61B 18/12* (2006.01)
*A61B 5/04* (2006.01)
(Continued)

(52) U.S. Cl.
CPC ........ *A61B 5/04001* (2013.01); *A61B 5/4836* (2013.01); *A61B 5/6853* (2013.01);
(Continued)

(58) Field of Classification Search
CPC ...... A61B 18/1492; A61B 2018/00434; A61B 2018/00571; A61B 2018/1467;
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| EP | 1169976 | 1/2002 |
| EP | 2316371 | 5/2011 |

(Continued)

OTHER PUBLICATIONS

Curtis, J.J., et al., "Surgical therapy for persistent hypertension after renal transplantation." Transplantation, 1981, 31: 125-128.

(Continued)

*Primary Examiner* — Thomas A Giuliana

(57) ABSTRACT

Neuromodulation systems with nerve monitoring assemblies and associated devices, systems, and methods are disclosed herein. A neuromodulation system configured in accordance with some embodiments of the present technology can include, for example, a generator, a nerve monitoring assembly configured to detect electroneurogram (ENG) signals, and a neuromodulation catheter. The neuromodulation catheter can include an elongated shaft with a distal portion and a proximal portion. The distal portion of the shaft can include an array of electrodes configured to detect nerve activity from within a blood vessel of a human. The proximal portion of the shaft can include at least one connector that operably couples the electrodes to the generator and to the nerve monitoring assembly.

6 Claims, 13 Drawing Sheets

(51) Int. Cl.
*A61B 17/32* (2006.01)
*A61B 18/02* (2006.01)
*A61B 18/14* (2006.01)
*A61B 5/00* (2006.01)
*A61N 1/05* (2006.01)
*A61N 1/36* (2006.01)
*A61B 17/00* (2006.01)
*A61B 18/00* (2006.01)
*A61N 7/00* (2006.01)

(52) U.S. Cl.
CPC .......... *A61B 5/6858* (2013.01); *A61B 5/7203* (2013.01); *A61B 5/7225* (2013.01); *A61B 17/320068* (2013.01); *A61B 18/02* (2013.01); *A61B 18/1492* (2013.01); *A61N 1/0551* (2013.01); *A61N 1/36057* (2013.01); *A61N 1/36114* (2013.01); *A61N 1/36117* (2013.01); *A61N 1/36139* (2013.01); *A61B 5/0031* (2013.01); *A61B 2017/00039* (2013.01); *A61B 2018/0022* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00839* (2013.01); *A61B 2018/0212* (2013.01); *A61B 2018/1435* (2013.01); *A61B 2018/1467* (2013.01); *A61N 2007/006* (2013.01); *A61N 2007/0021* (2013.01); *A61N 2007/0043* (2013.01); *A61N 2007/0052* (2013.01)

(58) Field of Classification Search
CPC .. A61B 2018/1435; A61B 2018/00839; A61B 2018/00642; A61B 2018/00577; A61B 2018/0016; A61B 2018/00214; A61B 2018/0212; A61B 2018/0064; A61B 2018/00273; A61B 2018/00279; A61B 2018/00267; A61B 2018/00404; A61B 5/6858; A61B 5/04001; A61B 5/4836; A61B 5/6857; A61B 5/7203; A61N 1/36114; A61N 1/36117; A61N 1/0551; A61N 1/36057
USPC ........... 606/34, 41, 42; 607/98, 99, 115, 116
See application file for complete search history.

(56) References Cited

U.S. PATENT DOCUMENTS

| | | | |
|---|---|---|---|
| 4,709,698 A | 12/1987 | Johnston et al. | |
| 4,764,504 A | 8/1988 | Johnson et al. | |
| 4,890,623 A | 1/1990 | Cook et al. | |
| 4,976,711 A | 12/1990 | Parins et al. | |
| 5,300,068 A | 4/1994 | Rosar et al. | |
| 5,301,683 A | 4/1994 | Durkan | |
| 5,358,514 A | 10/1994 | Schulman et al. | |
| 5,368,591 A | 11/1994 | Lennox et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,772,590 A | 6/1998 | Webster, Jr. | |
| 5,860,974 A | 1/1999 | Abele et al. | |
| 5,865,787 A | 2/1999 | Shapland et al. | |
| 5,893,885 A | 4/1999 | Webster et al. | |
| 5,944,710 A | 8/1999 | Dev et al. | |
| 5,954,719 A | 9/1999 | Chen et al. | |
| 5,983,141 A | 11/1999 | Sluijter et al. | |
| 6,004,269 A | 12/1999 | Crowley et al. | |
| 6,009,877 A | 1/2000 | Edwards | |
| 6,024,740 A | 2/2000 | Lesh et al. | |
| 6,036,687 A | 3/2000 | Laufer et al. | |
| 6,066,134 A | 5/2000 | Eggers et al. | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,142,993 A | 11/2000 | Whayne et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,405,732 B1 | 6/2002 | Edwards et al. | |
| 6,413,255 B1 | 7/2002 | Stern | |
| 6,488,679 B1 | 12/2002 | Swanson et al. | |
| 6,506,189 B1 | 1/2003 | Rittman, III et al. | |
| 6,514,226 B1 | 2/2003 | Levin et al. | |
| 6,522,926 B1 | 2/2003 | Kieval et al. | |
| 6,542,781 B1 | 4/2003 | Koblish et al. | |
| 6,562,034 B2 | 5/2003 | Edwards et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,640,120 B1 | 10/2003 | Swanson et al. | |
| 6,685,648 B2 | 2/2004 | Flaherty et al. | |
| 6,711,444 B2 | 3/2004 | Koblish | |
| 6,736,835 B2 | 5/2004 | Pellegrino et al. | |
| 6,752,805 B2 | 6/2004 | Maguire et al. | |
| 6,845,267 B2 | 1/2005 | Harrison et al. | |
| 6,850,801 B2 | 2/2005 | Kieval et al. | |
| 6,869,431 B2 | 3/2005 | Maguire et al. | |
| 6,885,888 B2 | 4/2005 | Rezai | |
| 6,893,436 B2 | 5/2005 | Woodard et al. | |
| 6,939,346 B2 | 9/2005 | Kannenberg et al. | |
| 7,149,574 B2 | 12/2006 | Yun et al. | |
| 7,160,296 B2 | 1/2007 | Pearson et al. | |
| 7,162,303 B2 | 1/2007 | Levin et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 7,805,195 B2 * | 9/2010 | Zealear .................. A61B 5/087 607/42 |
| 7,949,398 B1 | 5/2011 | Wenzel et al. | |
| 8,131,371 B2 | 3/2012 | Demarais et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 8,702,619 B2 | 4/2014 | Wang | |
| 8,768,470 B2 | 7/2014 | Deem et al. | |
| 8,909,316 B2 | 12/2014 | Ng | |
| 8,977,359 B2 | 3/2015 | Rossing | |
| 9,002,446 B2 | 4/2015 | Wenzel et al. | |
| 9,014,809 B2 | 4/2015 | Wenzel et al. | |
| 9,014,821 B2 | 4/2015 | Wang | |
| 9,022,948 B2 | 5/2015 | Wang | |
| 9,119,600 B2 | 9/2015 | Richardson et al. | |
| 9,168,094 B2 | 10/2015 | Lee et al. | |

(56) References Cited

U.S. PATENT DOCUMENTS

| | | |
|---|---|---|
| 9,179,973 B2 | 11/2015 | Nabutovsky et al. |
| 9,186,212 B2 | 11/2015 | Nabutovsky et al. |
| 9,295,842 B2 | 3/2016 | Ghaffari et al. |
| 9,314,300 B2 | 4/2016 | Nabutovsky et al. |
| 9,326,816 B2 * | 5/2016 | Srivastava ..... A61B 17/320068 |
| 9,375,154 B2 | 6/2016 | Wang |
| 9,427,283 B2 | 8/2016 | Nabutovsky et al. |
| 9,427,579 B2 | 8/2016 | Fain et al. |
| 9,554,850 B2 | 1/2017 | Lee et al. |
| 9,579,030 B2 | 2/2017 | Scheuermann et al. |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danek et al. |
| 2004/0010289 A1 | 1/2004 | Biggs et al. |
| 2004/0167509 A1 | 8/2004 | Taimisto |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan |
| 2006/0206150 A1 | 9/2006 | Demarais et al. |
| 2006/0212076 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0112400 A1 | 5/2011 | Emery et al. |
| 2011/0270120 A1 | 11/2011 | McFarlin et al. |
| 2011/0306851 A1 * | 12/2011 | Wang ................ A61N 1/36114 600/301 |
| 2011/0307034 A1 | 12/2011 | Hastings et al. |
| 2012/0029504 A1 | 2/2012 | Afonso et al. |
| 2012/0116382 A1 | 5/2012 | Ku et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0143097 A1 | 6/2012 | Pike, Jr. |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0265198 A1 | 10/2012 | Crow et al. |
| 2012/0296232 A1 | 11/2012 | Ng |
| 2012/0296329 A1 | 11/2012 | Ng |
| 2013/0085489 A1 | 4/2013 | Fain et al. |
| 2013/0123778 A1 | 5/2013 | Richardson et al. |
| 2013/0131743 A1 | 5/2013 | Yamasaki et al. |
| 2013/0165764 A1 | 6/2013 | Scheuermann et al. |
| 2013/0172878 A1 | 7/2013 | Smith |
| 2013/0218029 A1 | 8/2013 | Cholette et al. |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0012242 A1 | 1/2014 | Lee et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0288551 A1 | 9/2014 | Bharmi et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0018656 A1 | 1/2015 | Min et al. |
| 2015/0025524 A1 | 1/2015 | Nabutovsky |
| 2015/0066007 A1 * | 3/2015 | Srivastava ..... A61B 17/320068 606/21 |
| 2015/0112329 A1 | 4/2015 | Ng |
| 2015/0119674 A1 | 4/2015 | Fischell et al. |
| 2015/0173673 A1 | 6/2015 | Toth et al. |
| 2015/0201997 A1 | 7/2015 | Osypka |
| 2015/0216590 A1 | 8/2015 | Wang et al. |
| 2015/0223877 A1 | 8/2015 | Behar et al. |
| 2015/0224326 A1 | 8/2015 | Toth et al. |
| 2015/0289770 A1 | 10/2015 | Wang |
| 2015/0289929 A1 | 10/2015 | Toth et al. |
| 2015/0366609 A1 | 12/2015 | Richardson et al. |
| 2016/0000345 A1 | 1/2016 | Kobayashi et al. |
| 2016/0015452 A1 | 1/2016 | Nabutovsky et al. |
| 2016/0029960 A1 | 2/2016 | Toth et al. |
| 2016/0038028 A1 | 2/2016 | Buelna et al. |
| 2016/0081744 A1 | 3/2016 | Wang |
| 2016/0095652 A1 | 4/2016 | Lee et al. |
| 2016/0106498 A1 | 4/2016 | Highsmith et al. |
| 2016/0184010 A1 | 6/2016 | Nabutovsky et al. |
| 2016/0213262 A1 | 7/2016 | Ghaffari et al. |
| 2016/0213424 A1 | 7/2016 | Ghaffari et al. |
| 2016/0324572 A1 | 11/2016 | Gross et al. |
| 2016/0331451 A1 | 11/2016 | Nabutovsky et al. |
| 2016/0331453 A1 | 11/2016 | Fain et al. |
| 2016/0374568 A1 | 12/2016 | Wang |
| 2017/0215950 A1 | 8/2017 | Gross et al. |

FOREIGN PATENT DOCUMENTS

| | | |
|---|---|---|
| EP | 2594193 | 5/2013 |
| EP | 2613704 | 7/2013 |
| EP | 2747691 | 7/2014 |
| EP | 2797535 | 11/2014 |
| EP | 2852339 | 4/2015 |
| EP | 2866645 | 5/2015 |
| EP | 2887900 | 7/2015 |
| EP | 2907464 | 8/2015 |
| EP | 2914334 | 9/2015 |
| EP | 2967383 | 1/2016 |
| EP | 2978372 | 2/2016 |
| EP | 3011899 | 4/2016 |
| EP | 3028628 | 6/2016 |
| EP | 3089686 | 11/2016 |
| EP | 2709517 | 1/2017 |
| JP | H08504531 | 5/1996 |
| JP | H1071037 | 3/1998 |
| JP | 2001518808 | 10/2001 |
| JP | 2005278739 | 10/2005 |

(56) References Cited

FOREIGN PATENT DOCUMENTS

| | | |
|---|---|---|
| JP | 2008515544 | 5/2008 |
| JP | 2009539565 | 11/2009 |
| JP | 2010162163 | 7/2010 |
| JP | 2010533513 | 10/2010 |
| JP | 2011505929 | 3/2011 |
| WO | WO-2014091328 | 7/1989 |
| WO | WO-199407446 | 4/1994 |
| WO | WO-1995025472 | 9/1995 |
| WO | WO-9531142 | 11/1995 |
| WO | WO-1997036548 | 10/1997 |
| WO | WO1998042403 | 10/1998 |
| WO | WO-9900060 | 1/1999 |
| WO | WO-9900060 | 7/1999 |
| WO | WO-2001022897 | 4/2001 |
| WO | WO-2001070114 | 9/2001 |
| WO | WO-2003022167 | 3/2003 |
| WO | WO-2003/082080 | 10/2003 |
| WO | WO-2005030072 | 4/2005 |
| WO | WO-2005041748 | 5/2005 |
| WO | WO-2005/110528 | 11/2005 |
| WO | WO2006041881 | 4/2006 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO2008003058 | 1/2008 |
| WO | WO-2008049084 | 4/2008 |
| WO | WO-2010078175 | 7/2010 |
| WO | WO2011089935 | 7/2011 |
| WO | WO-2012033974 | 3/2012 |
| WO | WO2012068471 | 5/2012 |
| WO | WO-2012158864 | 11/2012 |
| WO | WO-2013030738 | 3/2013 |
| WO | WO-2013030743 | 3/2013 |
| WO | WO-2013074813 | 5/2013 |
| WO | WO-2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014091401 | 6/2014 |
| WO | WO-2014/149550 | 9/2014 |
| WO | WO-2014/149552 | 9/2014 |
| WO | WO-2014/149553 | 9/2014 |
| WO | WO-2014/149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014/158713 | 10/2014 |
| WO | WO-2014158708 | 10/2014 |
| WO | WO-2014163990 | 10/2014 |
| WO | WO-2014/179768 | 11/2014 |
| WO | WO-2014/182946 | 11/2014 |

OTHER PUBLICATIONS

Dibona, G.F., et al. "Neural control of renal function." Physiol Rev, 77:75-197 (1997).
Smithwick et al., "Splanchnicectomy for essential hypertension." J. Am. Med. Assn. 152:16 (1953), pp. 1501-1504.
Final Office Action; U.S. Appl. No. 12/827,700; dated Feb. 5, 2013, 61 pages.
Valente, J.F. "Laparoscopic renal denervation for intractable ADPKD-related pain." Nephrol Dial Transplant, 16: 160 (2001).
Demosthenous et al., "A Programmable ENG amplifier with passive EMG neutralization for FES applications", Circuits and Systems, May 18, 2008. ISCAS 2008, 1552-1555.
Demosthenous et al. "An Adaptive ENG Amplifier for Tripolar Cuff Electrodes", IEEE Journal of Solid-State Circuits, vol. 40, No. 2, Feb. 1, 2005, 412-421.
International Search Report and Written Opinion for International Application No. PCT/US2014/053210, dated Nov. 5, 2014, 12 pages.
European Search Report for European Application No. 13159256, dated Oct. 17, 2013, 6 pages.
Allen, E.V., Sypathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus." The Pain Clinic, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1963, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertention." New England Journal of Med. Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essentiai Hypertension," J. Clin Invest 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 64:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Cathether-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2014, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

(56) References Cited

OTHER PUBLICATIONS

Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Chinushi et al., "Blood Pressure and Autonomic Responses to Electrical Stimulation of the Renal Arterial Nerves Before and After Ablation of the Renal Artery." Hypertention, 2013, 61, pp. 450-456.
Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999: 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0.8816.2103278.00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping," Journal of Applied Physiology, 1991, vol. 71, No. 4, pp. 1529-1539.
Prochnau, Dirk et al., Catheter-based renal denervation for drug-resistant hypertension by using a standard electrophysiology catheter, Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol, 93, Jun. 1, 2004, 4 pages.
Purerfellner, Helmet et al., Pulmonary Vein Stenosis Following Catheter Ablation of Atrial Fibrillation, Curr. Opin. Cardio. 20 : 484-490, 2005.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 60/852,787, filed Oct. 18, 2006, 112 pages.
Wittkampf et al., "Control fo radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension," PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year," Cleveland Clinic, Oct. 6, 2011, 2 pages, <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news-latest-news/does-renal-denervation-represent-a-new-treatment-option-for-resistant-hypertension>.
"Iberis—Renal Sympathetic Denervation System: Turning innovation into quality care." [Brochure], Terumo Europe N.V. 2013, Europe, 3 pages.
"Neurotech Reports Announces Winners of Gold Electrode Awards." Neurotech business report, 2009, 1 page. <http//www.neurotechreports.com/pages/goldelectrodes09.html>.
"Quick, Consistent, Controlled, OneShot renal Denervation System" [Brochure], Covidien: positive results for life, 2013, (n.l.), 4 pages.

(56) References Cited

OTHER PUBLICATIONS

"Renal Denervation Technology of Vessix Vascular, Inc. been acquired by Boston Scientific Corporation (BSX) to pay up to $425 Million," Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1996, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, 2013, No. 3, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol. 2:285-292 (1998).
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, http://www.fastcompany.com/3007645/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery ebolization with diluted hot contrast medium: An experimental study." J Vasc Intern Radiol, 12: 862-858 (2001).

Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation," EuroIntervention, vol. 9, 2013, 9 pages.
Huang et al., "Renal denervation prevents and reverses hyperinsulinemia-Induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al., "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patents With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial," EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchniceotomy" Am J Surgery (1948) pp. 46-68.
Renal Denervation (RDN), Symplicity RDN System Common Q&A (2011), 4 pages, http://www.medtronic.com/rdn/mediakit/RDN%20FAQ.pdf.

(56) References Cited

OTHER PUBLICATIONS

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on Interventional therapy of resistant hypertension." EuroIntervention, vol. 9, 2013, 9 pages.

Sievert, Horst, "Novelty Award EuroPCR 2010," Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertention," Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen "The St. Jude Renal Denervation System Tecnnology and Clinical Review." The University of Adelaide Australia, 2012, 24 pages.

Zuern, Christine S. "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Miller, Reed, "Finding a Future for Renal Denervation With Better Controlled Trials." Pharma & Medtech Business Intelligence, Article #01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014: 115: 211-214.

Papademetriou, Vasilios et al., "Renal Nerve Ablation for Resistant Hypertension: How Did We Get Here, Present Status, and Future Directions." Circulation. 2014: 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension, 2014: 64: 565-572.

Doumas, Michael et al., "Renal Nerve Ablation for Resistant Hypertension: The Dust Has Not Yet Settled." The Journal of Clinical Hypertension. 2014: vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.

Opposition to European Patent No. 2465470, Granted Oct. 28, 2015, Date of Opposition Jul. 27, 2016, 34 pages.

U.S. Appl. No. 11/363,867, filed Feb. 27, 2006, 70 pages.

U.S. Appl. No. 60/813,589, filed Dec. 29, 2005, 62 pages.

Ureter, https://en.wikipedia.org/wiki/Ureter, Jun. 2016, 6 pages.

\* cited by examiner

NEUROMODULATION SYSTEMS HAVING NERVE MONITORING ASSEMBLIES AND ASSOCIATED DEVICES, SYSTEMS, AND METHODS

RELATED APPLICATIONS

This application is a Continuation of and claims the benefit of U.S. patent application Ser. No. 14/015,793, filed Aug. 30, 2013, now U.S. Pat. No. 9,326,816, the disclosure of which is herein incorporated by reference in its entirety.

TECHNICAL FIELD

The present technology is related to neuromodulation systems. In particular, at least some embodiments are related to neuromodulation systems having nerve monitoring assemblies.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Neuromodulation devices configured in accordance with at least some embodiments of the present technology can include energy delivery elements or other contacts that are part of a neuromodulation assembly and configured to detect neural signals before and/or after neuromodulation. Specific details of several embodiments of the present technology are described herein with reference to FIGS. 1-14B. Although many of the embodiments are described with respect to devices, systems, and methods for intravascular renal neuromodulation, other applications and other embodiments in addition to those described herein are within the scope of the present technology. For example, at least some embodiments may be useful for intraluminal neuromodulation, for extravascular neuromodulation, for non-renal neuromodulation, and/or for use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation device). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

I. SELECTED EXAMPLES OF NEUROMODULATION DEVICES AND RELATED SYSTEMS

Figure 1:
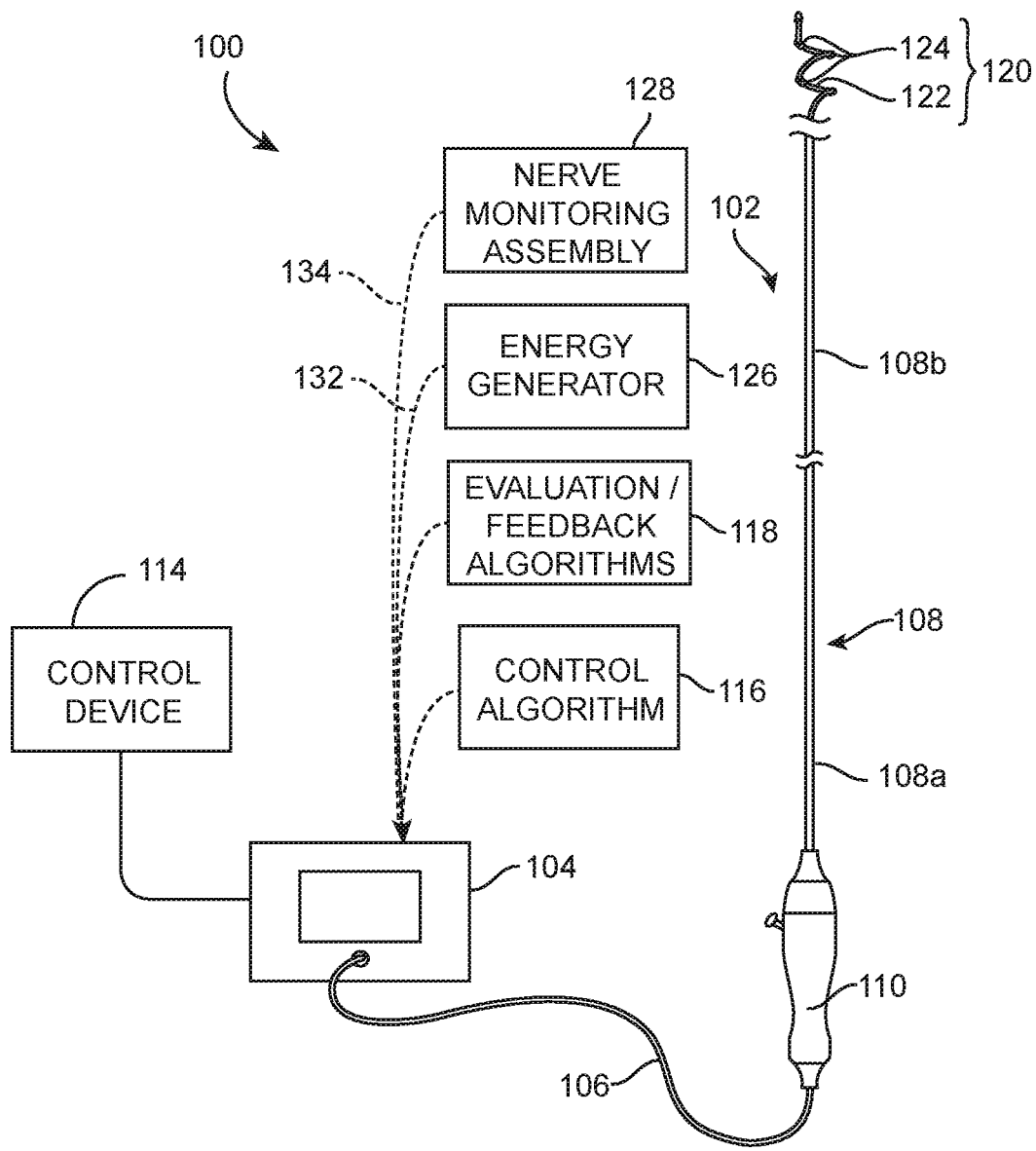
FIG. 1 is a partially schematic illustration of a neuromodulation system including a neuromodulation catheter configured in accordance with an embodiment of the present technology.

FIG. 1 is a partially schematic illustration of a therapeutic system 100 ("system 100") configured in accordance with an embodiment of the present technology. The system 100 can include a neuromodulation catheter 102, a console 104, and a cable 106 extending therebetween. The neuromodulation catheter 102 can include an elongated shaft 108 having a proximal portion 108a and a distal portion 108b. The shaft 108 and the neuromodulation assembly 120 can be 2, 3, 4, 5, 6, or 7 French or one or more other suitable sizes. A handle 110 of the neuromodulation catheter 102 can be operably connected to the shaft 108 via the proximal portion 108a, and a neuromodulation assembly 120 can be operably connected to the shaft 108 via the distal portion 108b. The neuromodulation assembly 120 can include a support structure 122 and an array of two or more contacts and/or energy delivery elements 124 (e.g., electrodes). In the illustrated embodiment, the support structure 122 has a spiral/helical arrangement. However, other neuromodulation assemblies may have different structural configurations and/or include energy delivery elements other than electrodes.

The shaft 108 can be configured to locate the neuromodulation assembly 120 intravascularly at a target site within or otherwise proximate to a body lumen (e.g., a blood vessel, a duct, an airway, or another naturally occurring lumen within the human body). In certain embodiments, intravascular delivery of the neuromodulation catheter 102 includes percutaneously inserting a guide wire (not shown) into a body lumen of a patient and moving the shaft 108 and/or the neuromodulation assembly 120 along the guide wire until the neuromodulation assembly 120 reaches a target site (e.g., a renal artery). In certain embodiments, for example, the distal end of the neuromodulation assembly 120 may define a passageway for engaging the guide wire for delivery of the neuromodulation assembly 120 using over-the-wire (OTW) or rapid exchange (RX) techniques. In other embodiments, the neuromodulation catheter 102 can be a steerable or non-steerable device configured for use without a guide wire. In still other embodiments, the neuromodulation catheter 102 can be configured for delivery via a guide catheter or sheath (not shown).

Once at the target site, the neuromodulation assembly 120 can be configured to detect neural signals proximate to the target site by recording electrical activity of neurons proximate to the target site using the energy delivery elements 124 and/or other contacts. The neuromodulation assembly 120 can also be configured to provide or facilitate a neuromodulation treatment at the target site (e.g., a treatment location within the renal arteries) using various modalities (e.g., RF ablation, cryotherapeutic cooling, ultrasound radiation, etc.). As explained in further detail below, the neuromodulation assembly 120 can record nerve activity before and/or after neuromodulation treatment to determine the effectiveness of the neuromodulation treatment.

The console 104 can be configured to control, monitor, supply, and/or otherwise support operation of the neuromodulation catheter 102. The console 104 can further be configured to generate a selected form and/or magnitude of energy for delivery to tissue at the target site via the neuromodulation assembly 120 (e.g., via the energy delivery elements 124). The console 104 can have different configurations depending on the treatment modality of the neuromodulation catheter 102. For example, when the neuromodulation catheter 102 is configured for electrode-based, heat-element-based, or transducer-based treatment, the console 104 can include an energy generator 126 (shown schematically) configured to generate radio frequency (RF) energy (e.g., monopolar and/or bipolar RF energy), pulsed energy, microwave energy, optical energy, ultrasound energy (e.g., intravascularly delivered ultrasound, extracorporeal ultrasound, and/or high-intensity focused ultrasound (HIFU)), direct heat energy, radiation (e.g., infrared, visible, and/or gamma radiation), and/or another suitable type of energy. When the neuromodulation catheter 102 is configured for cryotherapeutic treatment, the console 104 can include a refrigerant reservoir (not shown), and can be configured to supply the neuromodulation catheter 102 with refrigerant. Similarly, when the neuromodulation catheter 102 is configured for chemical-based treatment (e.g., drug infusion), the console 104 can include a chemical reservoir (not shown) and can be configured to supply the neuromodulation catheter 102 with one or more chemicals.

In selected embodiments, the system 100 may be configured to deliver a monopolar electric field via one or more of the energy delivery elements 124. In such embodiments, a neutral or dispersive electrode 130 (FIG. 2) may be electrically connected to the generator 126 and attached to the exterior of the patient. In embodiments including multiple energy delivery elements 124, the energy delivery elements 124 may deliver power independently (i.e., may be used in a monopolar fashion), either simultaneously, selectively, or sequentially, and/or may deliver power between any desired combination of the energy delivery elements 124 (i.e., may be used in a bipolar fashion). In addition, an operator optionally may be permitted to choose which energy delivery element(s) 124 are used for power delivery in order to form highly customized lesion(s) within the renal artery, as desired. Additionally, one or more sensors (not shown), such as one or more temperature (e.g., thermocouple, thermistor, etc.), impedance, pressure, optical, flow, chemical, neural signal, and/or other sensors, may be located proximate to, within, or integral with the energy delivery elements 124. The sensor(s) and the energy delivery elements 124 can be connected to one or more supply wires (not shown) that transmit signals from the sensor(s) and/or convey energy to the energy delivery elements 124.

As further shown in FIG. 1, the console 104 can also include a nerve monitoring assembly 128 (shown schematically) that is configured to detect electroneurogram (ENG) signals based on recordings of electrical activity of neurons taken by the energy delivery elements 124 or other contacts of the neuromodulation assembly 120. In the embodiment illustrated in FIG. 1, the nerve monitoring assembly 128 and the generator 126 are integrated into a single component, i.e., the console 104. In other embodiments, the nerve monitoring assembly 128 and the generator 126 can be separate components. The nerve monitoring assembly 128 can be operably coupled to the energy delivery elements 124 and/or other contacts at the distal portion 108b of the catheter 102 via signal wires (e.g., copper wires) that extend through the cable 106 and through the length of the shaft 108. In other embodiments, the energy delivery elements 124 can be communicatively coupled to the nerve monitoring assembly 128 using other suitable communication means. As explained in further detail below, the nerve monitoring assembly 128 can distinguish the ENG signals from other signals (e.g., electromyogram (EMG) signals) in the electrical activity recorded by energy delivery elements 124. The ENG signals can then be used to make various determinations related to the nerves proximate to the target site, such as whether a neuromodulation treatment was effective in ablating the nerves at the target site.

In embodiments where the energy delivery elements 124 both record neural signals and deliver energy, the energy delivery elements 124 can be operably connected to one or more connectors. For example, a first connector 132 can operably couple the energy delivery elements 124 to the generator 126 to deliver energy to the energy delivery elements 124, and a second connector 134 can operably couple the energy delivery elements 124 to the nerve monitoring assembly 128 to provide a recording function. When the nerve monitoring assembly 128 and the generator 126 are integrated into a single unit (e.g., the console 104 illustrated in FIG. 1), the proximal portion 108a of the shaft 108 can be connected to the console 104, and the first and second connectors 132 and 134 can be separate connection lines within the console 104. For example, the console 104 can also or alternatively include a switching circuit that connects the energy delivery elements 124 to either the generator 126 or to the nerve monitoring assembly 128 depending on the desired function the neuromodulation assembly 120 (e.g., nerve monitoring or nerve recording). In certain embodiments, the console 104 can be configured to automatically switch between the generator 126 and the nerve monitoring assembly 128, and in other embodiments this task can be performed manually (e.g., by an operator). In other embodiments (e.g., when the generator 126 and the nerve monitoring assembly 128 are separate components), the first and second connectors 132 and 134 can be positioned at the proximal portion 108a of the shaft 108, in the handle 110, at the proximal portion the cable 106, and/or at other portions of the system 100. In further embodiments, the cable 106, the handle 110, and/or the proximal portion 108a of the shaft 108 can include a single connector that can be plugged into the nerve monitoring assembly 128 during nerve monitoring and then plugged into to the generator 126 during energy delivery. In this embodiment, the cable 106, the handle 110, and/or the shaft 108 can include a switching circuit that connects the energy delivery elements 124 to the generator 126 or to the nerve monitoring assembly 128 depending on the function the neuromodulation assembly 120 is performing. This change in connection can be performed manually or automatically. For example, the neuromodulation catheter 102 can detect whether it is connected to the nerve monitoring assembly 128 or the generator 126, and provide the correct connection to the neuromodulation assembly 120.

In various embodiments, the system 100 can further include a control device 114 communicatively coupled to the neuromodulation catheter 102. The control device 114 can be configured to initiate, terminate, and/or adjust operation of one or more components (e.g., the energy delivery elements 124) of the neuromodulation catheter 102 directly and/or via the console 104. In other embodiments, the control device 114 can be omitted or have other suitable locations (e.g., within the handle 110, along the cable 106, etc.). The console 104 can be configured to execute an automated control algorithm 116 and/or to receive control instructions from an operator. Further, the console 104 can be configured to provide feedback to an operator before, during, and/or after a treatment procedure via an evaluation/feedback algorithm 118.

Figure 2:
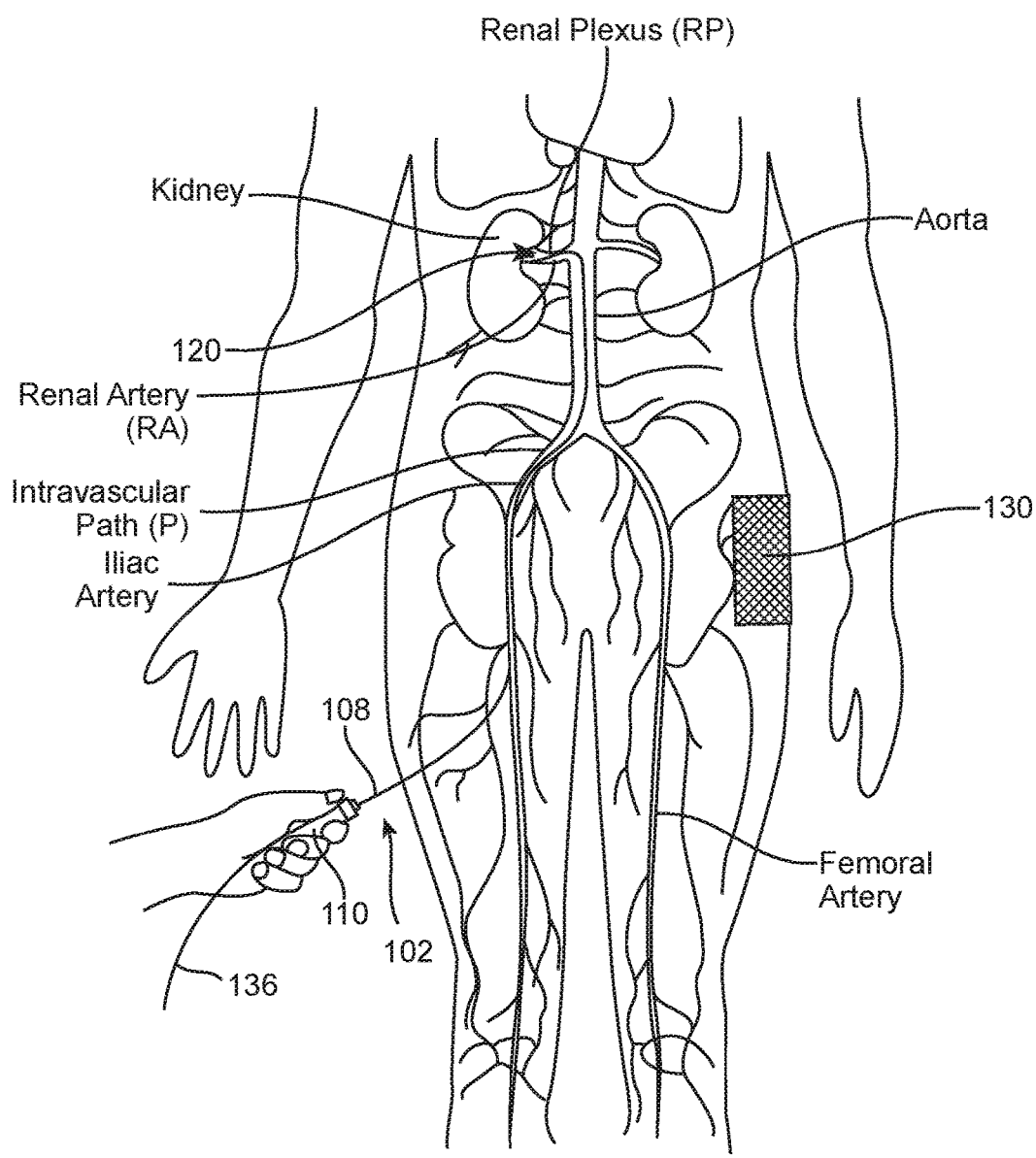
FIG. 2 illustrates monitoring and/or modulating renal nerves with the neuromodulation catheter of FIG. 1 in accordance with an embodiment of the present technology.

FIG. 2 (with additional reference to FIG. 1) illustrates modulating renal nerves in accordance with an embodiment of the system 100. The neuromodulation catheter 102 provides access to the renal plexus RP through an intravascular path P, such as a percutaneous access site in the femoral (illustrated), brachial, radial, or axillary artery to a targeted treatment site within a respective renal artery RA. By manipulating the proximal portion 108a of the shaft 108 from outside the intravascular path P, a clinician may advance the shaft 108 through the sometimes tortuous intravascular path P and remotely manipulate the distal portion 108b (FIG. 1) of the shaft 108. In the embodiment illustrated in FIG. 2, the neuromodulation assembly 120 is delivered intravascularly to the treatment site using a guide wire 136 in an OTW technique. As noted previously, the distal end of the neuromodulation assembly 120 may define a passageway for receiving the guide wire 136 for delivery of the neuromodulation catheter 120 using either OTW or RX techniques. At the treatment site, the guide wire 136 can be at least partially withdrawn or removed, and the neuromodulation assembly 120 can transform or otherwise be moved to a deployed arrangement for recording neural activity and/or delivering energy at the treatment site. In other embodiments, the neuromodulation assembly 120 may be delivered to the treatment site within a guide sheath (not shown) with or without using the guide wire 136. When the neuromodulation assembly 120 is at the target site, the guide sheath may be at least partially withdrawn or retracted and the neuromodulation assembly 120 can be transformed into the deployed arrangement. In still other embodiments, the shaft 108 may be steerable itself such that the neuromodulation assembly 120 may be delivered to the treatment site without the aid of the guide wire 136 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 120. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 120. Further, in some embodiments, image guidance components (e.g., IVUS, OCT) may be integrated with the neuromodulation catheter 102 and/or run in parallel with the neuromodulation catheter 102 to provide image guidance during positioning of the neuromodulation assembly 120. For example, image guidance components (e.g., IVUS or OCT) can be coupled to the neuromodulation assembly 120 to provide three-dimensional images of the vasculature proximate the target site to facilitate positioning or deploying the multi-electrode assembly within the target renal blood vessel.

The purposeful application of energy (e.g., RF energy) from the energy delivery elements 124 (FIG. 1) may then be applied to target tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements 124 (FIG. 1) and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

As described in greater detail below, hypothermic effects may also provide neuromodulation. Cryotherapy, for example, may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

Portions of the neuromodulation assembly 120 (e.g., the energy delivery elements 124 of FIG. 1 and/or other contacts) can intravascularly detect electrical signals before and/or after neuromodulation energy is applied to the renal artery. This information can then be filtered or otherwise processed by the nerve monitoring assembly 128 (FIG. 1) to differentiate the neural activity from other electrical signals (e.g., smooth cells/muscle signals), and the resultant ENG signals can be used to determine whether the neuromodulation treatment was effective. For example, statistically meaningful decreases in the ENG signal(s) taken after neuromodulation can serve as an indicator that the nerves were sufficiently ablated. Statistically meaningful decreases or drops in ENG signals generally refers to measurable or noticeable decreases in the ENG signals.

II. SELECTED EMBODIMENTS OF NERVE MONITORING ASSEMBLIES AND NEUROMODULATION ASSEMBLIES

Figure 3A:
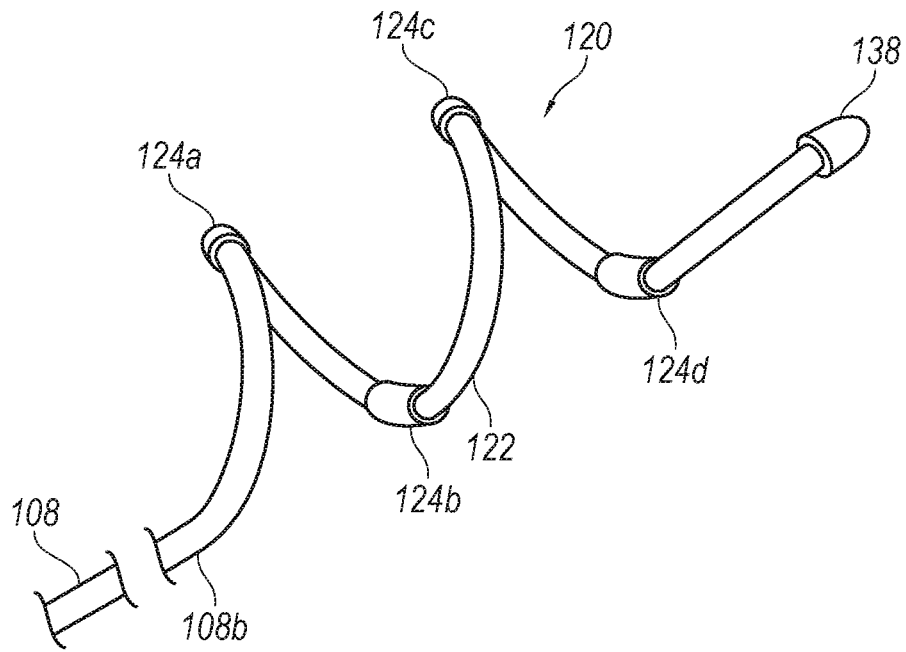
FIG. 3A is an enlarged isometric view of a distal portion of the neuromodulation catheter of FIG. 1 configured in accordance with an embodiment of the present technology.
Figure 3B:
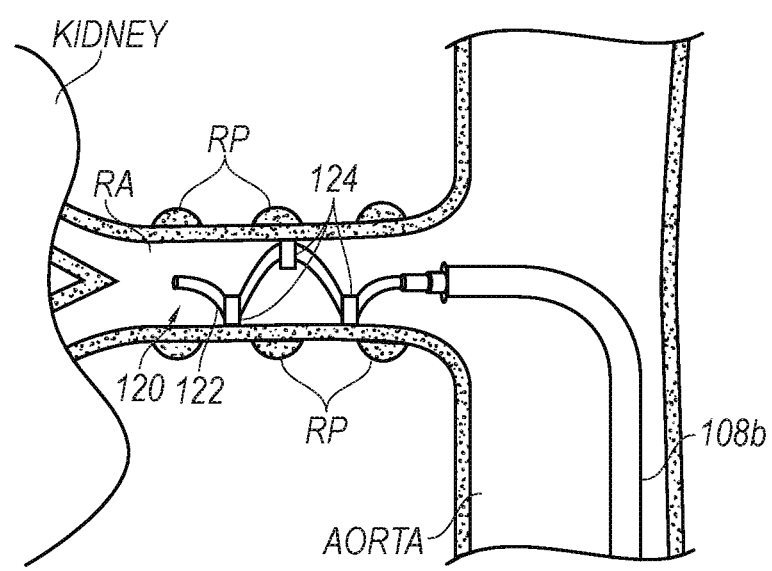
FIG. 3B is a side view of the distal portion of the neuromodulation catheter of FIG. 3A within a blood vessel in accordance with an embodiment of the present technology.

FIG. 3A is an enlarged isometric view of the neuromodulation assembly 120 of the neuromodulation catheter 102 of FIG. 1 configured in accordance with an embodiment of the present technology, and FIG. 3B is a side view of the neuromodulation assembly 120 of FIG. 3A within a renal artery RA in accordance with an embodiment of the present technology. As shown in FIG. 3A, the neuromodulation assembly 120 can include an array of four energy delivery elements 124 (identified individually as first through fourth energy delivery elements 124a-d, respectively) defined by electrodes and arranged along the length of the support member 122. In other embodiments the neuromodulation assembly may include a different number of energy delivery elements 124 (e.g., 1, 2, 8, 12, etc. energy delivery elements 124) arranged along the length of the support member 122. In further embodiments, one or more of the energy delivery elements 124 can have other suitable structures (e.g., ultrasound transducers, radiation emitters, etc.) for delivering various forms of energy to a treatment site within a body lumen (e.g., a blood vessel) and/or recording neural activity proximate thereto.

The support member 122 can be made from various different types of materials (e.g., metals and/or polymers) suitable for supporting the energy delivery elements 124. In the illustrated embodiment, the support member 122 has a helical shape in the deployed state. The dimensions (e.g., outer diameter and length) of the helical support member 122 can be selected to accommodate the vessels or other body lumens in which the neuromodulation assembly 120 is designed to be delivered. For example, the axial length of the deployed support member 122 may be selected to be no longer than a patient's renal artery (e.g., typically less than 7 cm), and have a diameter that accommodates the inner diameter of a typical renal artery RA (e.g., about 2-10 mm). In other embodiments, the support member 122 can have other dimensions depending on the body lumen within which it is configured to be deployed. In further embodiments, the support member 122 can have other suitable shapes (e.g., semi-circular, curved, straight, etc.), and/or the neuromodulation assembly 120 can include multiple support members 122 configured to carry one or more energy delivery elements 124. The support member 122 may be designed to apply a desired outward radial force to a vessel when expanded to a deployed state (shown in FIG. 1) to place the energy delivery element 124 in contact with the inner surface of the vessel wall (e.g., a renal artery RA as shown in FIG. 3B).

As shown in FIG. 3A, the support member 122 can optionally terminate with an atraumatic (e.g., rounded) tip 138. The atraumatic tip 138 may reduce the risk of injuring the blood vessel as the helically-shaped support member 122 expands and/or as a delivery sheath is retracted from the neuromodulation assembly 120. The atraumatic tip 138 can be made from a polymer or metal that is fixed to the end of the structural element by adhesive, welding, crimping, overmolding, solder, and/or other suitable attachment mechanisms. In other embodiments, the atraumatic tip 138 may be made from the same material as the support member 122, and integrally formed therefrom (e.g., by machining or melting). In further embodiments, the distal end portion of the support member 122 may have a different configuration and/or features. For example, in some embodiments the tip 138 may comprise an energy delivery element and/or a radiopaque marker.

As discussed above, the energy delivery elements 124 can be configured to detect nerve activity from within a blood vessel of a human patient (e.g., the renal artery shown in FIG. 3B) and/or deliver a therapeutic energy to nerves proximate to the blood vessel. In various embodiments, for example, pairs of the energy delivery element 124 can be configured to provide multi-polar (e.g., bipolar) recording of nerve activity proximate to a target site in a vessel and/or deliver bipolar energy to nerves proximate to the target site. The energy delivery elements 124 can be paired in various different configurations, such as the first and second energy delivery elements 124a and 124b, the first and third energy delivery elements 124a and 124c, the first and fourth energy delivery elements 124a and 124d, the second and fourth energy delivery elements 124b and 124d, and/or other suitable pairs of energy delivery elements 124 depending on the number of energy delivery elements 124 on the neuromodulation assembly 120 and/or the configuration of the neuromodulation assembly 120. Multi-polar recording is expected to reduce noise that would otherwise be collected via a single electrode because differential amplification of multi-polar recordings can selectively amplify the difference in the signal (the nerve action potential, i.e., the electrical activity developed in a nerve cell during activity), while suppressing the common signal (e.g., the background noise).

In certain embodiments, the neural recordings taken from a first pair of energy delivery elements 124 can be compared with neural recordings taken from one or more other pairs of energy delivery elements 124. For example, the neural recordings taken from a first electrode pair consisting of the first and second energy delivery elements 124a and 124b can be compared with the neural recordings taken from electrode pairs consisting of the first and third energy delivery elements 124a and 124c and/or the first and fourth energy delivery elements 124a and 124d. In further examples, the neural recordings taken from the first and second energy delivery elements 124a and 124b can be compared with that taken from the third and fourth energy delivery elements 124c and 124d, and/or the neural recordings taken from the second and third energy delivery elements 124b and 124c can be compared with that taken from the third and fourth energy delivery elements 124c and 124d. In embodiments including more or less than four energy delivery elements 124, neural recordings taken from different electrode pairs can be compared with each other. Comparing the different neural recordings can provide a more complete understanding of the neural activity before and/or after therapeutic energy delivery, such as whether neuromodulation was more effective along a certain longitudinal segment of the vessel. The comparison of neural recordings taken from different electrode pairs can also determine if certain electrode pairs detect stronger, more consistent, or otherwise better neural signals than other electrode pairs. In other embodiments, the individual energy delivery elements 124 can record neural activity and/or deliver therapeutic energy in a monopolar fashion.

Each energy delivery element 124 can be operatively coupled to one or more signal wires (not shown; e.g., copper wires) to transmit recorded electrical signals, drive therapeutic energy delivery, and/or otherwise provide a signal to/from the energy delivery elements 124. The signal wires can extend along the body of the shaft 108 to a proximal end of the shaft 108 where the signal wires can be operatively connected to a signal processing console (e.g., the console 104 of FIG. 1) suitable for detecting neural recordings and/or providing energy for neural modulation.

In operation, the energy delivery elements 124 can first be positioned against the walls of a blood vessel when the neuromodulation assembly 120 is in a deployed state (e.g., as shown in FIG. 3B), and one or more of the energy delivery elements 124 can record electrical activity proximate to the vessel wall before delivering therapeutic energy to the tissue. This information can be transmitted (e.g., via the signal wires or wirelessly) to the nerve monitoring assembly 128 (FIG. 1), which can filter the recorded electrical signals to provide a baseline or reference ENG signal for determining whether subsequent neuromodulation is sufficient to provide a therapeutic effect. In certain embodiments, the neuromodulation assembly 120 can be moved proximally or distally along the length of the vessel to record neural signals at a plurality of locations along the vessel, and the recorded neural signals can be analyzed using various different decision metrics to determine a baseline ENG signal. For example, the recorded signals can be analyzed by integrating the recorded neural signals, omitting some recorded signals from consideration (e.g., when the recording appears abnormal or insufficient for consideration), averaging a plurality of the recorded neural signals (e.g., if they are similar), and/or weighting averages of the recorded signals to provide the baseline ENG signal. In one embodiment, for example, recordings can be taken from a plurality of electrode pairs (e.g., the first and second electrodes, the first and third electrodes, the first and fourth electrodes, the second and third electrodes, etc.), and compared with one another. If any of the electrode pairs record a signal that differs to a certain degree (e.g., a threshold percentage) from the signals recorded by the other electrode pairs, the outlier recordings can be discarded and the remaining recordings can be averaged or otherwise analyzed to determine the ENG signal. In other embodiments, the clearest signal of a plurality of signals taken from different electrode pairs may be used as the baseline ENG signal.

In various embodiments, one or more of the energy delivery elements 124 can be used to modulate nerves proximate to the treatment site at non-therapeutic energy levels, and one or more energy delivery elements 124 can be configured to record the resultant neural activity of the modulated nerves. For example, the first energy delivery element 124a can apply non-therapeutic levels of RF energy or another form of energy to a vessel wall sufficient to stimulate the nerves proximate to the vessel wall, and the second and third energy delivery elements 124b and 124c can record the action potentials of the nerves during or after delivery of the energy from the first energy delivery element 124a. This procedure may be used when the recorded signals alone (i.e., without additional stimuli) are insufficient to measure neural activity.

After an ENG signal has been obtained, the energy delivery elements 124 that were used to record nerve activity can subsequently be used to apply therapeutically-effective levels of energy (e.g., RF energy) to the vessel wall to modulate (e.g., ablate) the nerves proximate to the vessel wall. The energy can be delivered from an energy generator (e.g., the energy generator of FIG. 1) to the energy delivery elements 124 via the same signal wires used to transmit the recorded neural activity. In other embodiments, the energy delivery elements 124 can be coupled to separate signal wires that specifically transmit energy from the generator to the energy delivery elements 124.

After applying the neuromodulation energy, one or more of the energy delivery elements 124 can be used to record neural activity from within the vessel and obtain an ENG signal after neuromodulation. In other embodiments, selected energy delivery elements 124 or other contacts can be designated solely for recording, and other energy delivery elements can be designated for therapeutic energy delivery. As discussed above, the ENG signal can be determined from recordings at one or more locations within the vessel. The ENG signals taken before and after energy application can be compared to determine the effects of the neuromodulation. For example, decreases in the ENG signal (compared to the baseline ENG signal) may indicate therapeutically effective neuromodulation of the target nerves. In further embodiments, neural recordings can be taken from different electrode pairs to provide a better understanding of the efficacy of the neuromodulation along the length of the vessel. The degree of the decrease may be used as an indicator of the efficacy of the neuromodulation. A lack of an ENG signal after neuromodulation may be indicative of sufficient denervation (e.g., 60%, 70%, 80%, 90% denervation) of the nerves extending proximate to the vessel. Increases in the ENG signal may indicate that sufficient ablation was not achieved, or other factors unrelated to the ablation energy may cause increases in the ENG signal.

Figure 4A:
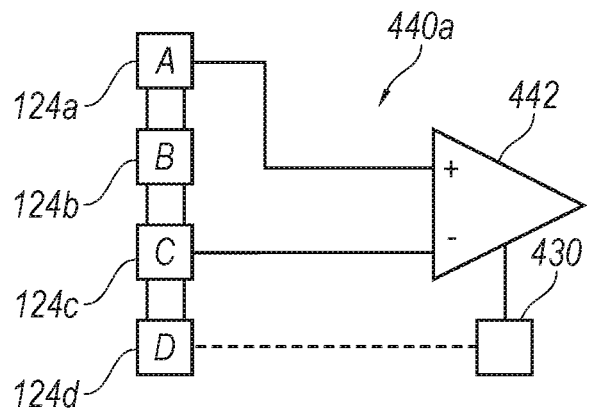
FIGS. 4A-4C are circuit diagrams of amplifier assemblies arranged in quasi-tripole (QT), true-tripole (TT), and adaptive or automatic tripole (AT) configurations, respectively, in accordance with embodiments of the present technology.
Figure 4B:
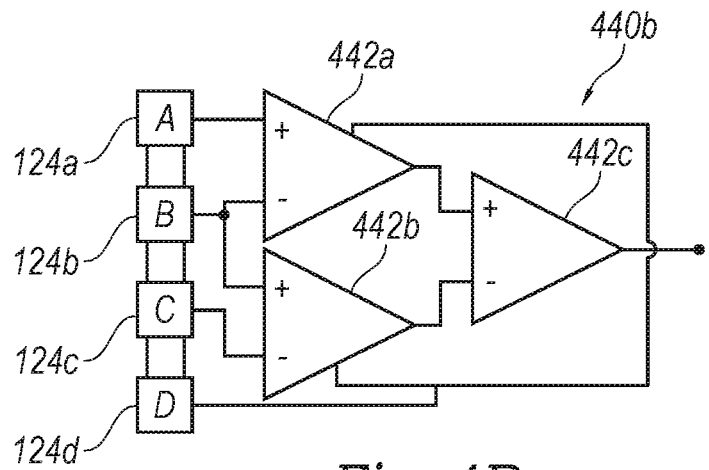
Figure 4C:
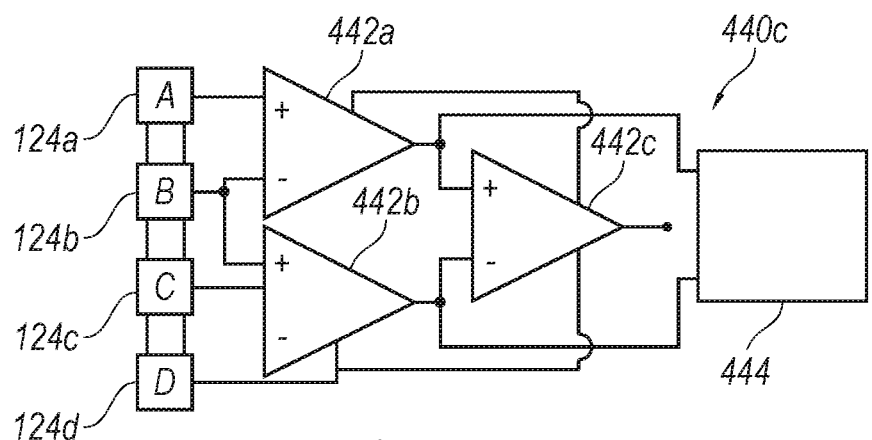

ENG recordings, which are typically on the order of micro volts (μV), may be degraded by interference signals that are typically generated from the muscles nearby (EMG signals on the order of several mV). However, as discussed above, the nerve monitoring assembly 128 of FIG. 1 can filter or otherwise process the signals recorded at the energy delivery elements 124 to at least substantially remove EMG signals or other signals from nearby muscles and/or other background noise that interferes with the ENG signals. FIGS. 4A-4C, for example, illustrate circuit diagrams of various amplifier assemblies (identified individually as first through third amplifier assemblies 440a-c, respectively, and referred to collectively as amplifier assemblies 440) for detecting the ENG signals from the recordings taken at the energy delivery elements 124. Referring to the embodiment illustrated in FIG. 4A, the first amplifier assembly 440a is arranged in a QT circuit in which two energy delivery elements 124 (e.g., the first and third energy delivery elements 124a and 124c) are electrically coupled to a differential amplifier 442. In other embodiments, a different pair of energy delivery elements 124 (e.g., the third and fourth energy delivery elements 124c and 124d) can be electrically coupled to the differential amplifier 442. The differential amplifier 442 can amplify the difference between the two energy delivery elements 124 connected thereto and, in doing so, is expected to at least substantially cancel out (e.g., minimize) EMG signals and other background noise common between the two energy delivery elements 124. The extent to which the QT amplifier assembly 440a can remove EMG signals depends at least in part on the energy delivery elements 124 being positioned symmetrically with respect to the vessel and the uniformity of the tissue (e.g., in thickness and consistency) in contact with the energy delivery elements 124. Two energy delivery elements (e.g., the second and fourth energy delivery elements 124b and 124d) can be shorted together to reduce the potential gradient and, therefore, the EMG interference detected by the energy delivery elements 124. One of the remaining energy delivery elements 124 (e.g., the second or fourth energy delivery element 124b or 124d) can serve as a reference or ground electrode. In other embodiments, another electrode 430 attached to the patient (e.g., the dispersive electrode 130 of FIG. 2) can serve as the reference electrode.

Referring to FIG. 4B, the second amplifier assembly 440b is arranged with the energy delivery elements 124 in a TT circuit. The TT circuit includes three differential amplifiers (identified individually as first through third differential amplifiers 442a-c, respectively, and referred to collectively as differential amplifiers 442). The first and second energy delivery elements 124a and 124b can be electrically coupled to the first differential amplifier 442a, and the second and third energy delivery elements 124b and 124c can be electrically coupled to the second differential amplifier 442b. The first and second differential amplifiers 442a and 442b can in turn be coupled to a double-differential amplifier, i.e., the third differential amplifier 442c. In this TT amplifier assembly 440b, the energy delivery elements 124 are each connected to an input of a differential amplifier (which has a high impedance load), and therefore the TT amplifier assembly 440b is insensitive to electrode impedance. This reduces phase differences caused by electrode capacitance, and therefore causes the TT amplifier assembly 440b to be unaffected by electrode mismatches (e.g., when the electrodes are not positioned symmetrically).

In various embodiments, the gain of first stage amplifiers defined by first and second differential amplifiers 442a and 442b can be manipulated to compensate for non-uniform readings from the two electrode pairs, such as the first and second energy delivery elements 124a and 124b and the second and third energy delivery elements 124b and 124c. For example, the first stage amplifiers 442a and 442b can be varied to compensate for non-uniform tissue contact between the electrode pairs 124a-b and 124b-c. A second stage differential amplifier defined by the third differential amplifier 442c can then be used to at least substantially cancel out EMG signals (e.g., by matching the equal in amplitude but opposite in phase EMG potential gradient at each half of the circuit). At the same time, the TT amplifier assembly 440b is expected to produce higher ENG signals (e.g., higher than the QT amplifier assembly 440a of FIG. 4A), and improve the ENG to EMG ratio by tuning of the gains (e.g., using low noise first stage differential amplifiers). In other embodiments, two different pairs of energy delivery elements 124 can be electrically coupled to the first stage differential amplifiers, and/or additional energy delivery elements can be coupled in pairs to differential amplifiers that are in turn electrically coupled to a subset of differential amplifiers. As with the QT circuit of FIG. 4A, the fourth energy delivery element 124d and/or another electrode can serve as a reference/ground electrode.

In FIG. 4C, the third amplifier assembly 440c is arranged with the energy delivery elements 124 in an AT circuit. Similar to the TT circuit, the AT circuit includes two pairs of energy delivery elements 124 (e.g., the first and second energy delivery elements 124a and 124b and the second and third energy delivery elements 124b and 124c) electrically coupled to two corresponding differential amplifiers 442 (i.e., the first and second differential amplifiers 442a and 442b), which are in turn coupled to the third differential amplifier 442c. In addition, the output of the first stage differential amplifiers (i.e., the first and second differential amplifiers 442a and 442b) are also electrically coupled to controller 444. The controller 444 can allow the AT circuit to automatically compensate for electrode errors using a closed-loop control approach (i.e., automatic feedback gain adjustment). For example, the controller 444 can include two additional variable gain amplifiers, two rectifiers, a comparator, an integrator, and a feedback amplifier to provide the desired automatic feedback gain adjustment. The AT amplifier assembly 440c applies a frequency independent method, and therefore is expected to reduce EMG interference and at the same time retain neural information at the ENG bandwidth of interest. As discussed above with regard to the QT and TT circuit configurations, the fourth energy delivery element 124d and/or another electrode can serve as a reference electrode, and/or the energy delivery elements 124 can be arranged in different pairs than those shown in FIG. 4C.

Any one of the amplifier assemblies 440 can be incorporated into a nerve monitoring assembly (e.g., the nerve monitoring assembly 128 of FIG. 1) to differentiate ENG signals from EMG signals and other background noise, and thereby detect neural activity. The detected ENG signals can be displayed on a screen, monitor, or other type of display in real-time for an operator (e.g., a physician) to view during and/or after a procedure. In other embodiments, ENG signals can be filtered from the EMG signals using analog or digital filtering applied to the output signal, and the filtered ENG signals can be used in conjunction with amplifier neutralization. In further embodiments, high-order filtering may be used to separate ENG signals from slower EMG signals because the frequency spectra of the two signals overlap, but the peaks of their power spectral densities differs by about an order of magnitude. In still further embodiments, algorithms and/or artificial neural networks can be used to separate ENG signals from EMG signals.

Figure 5:
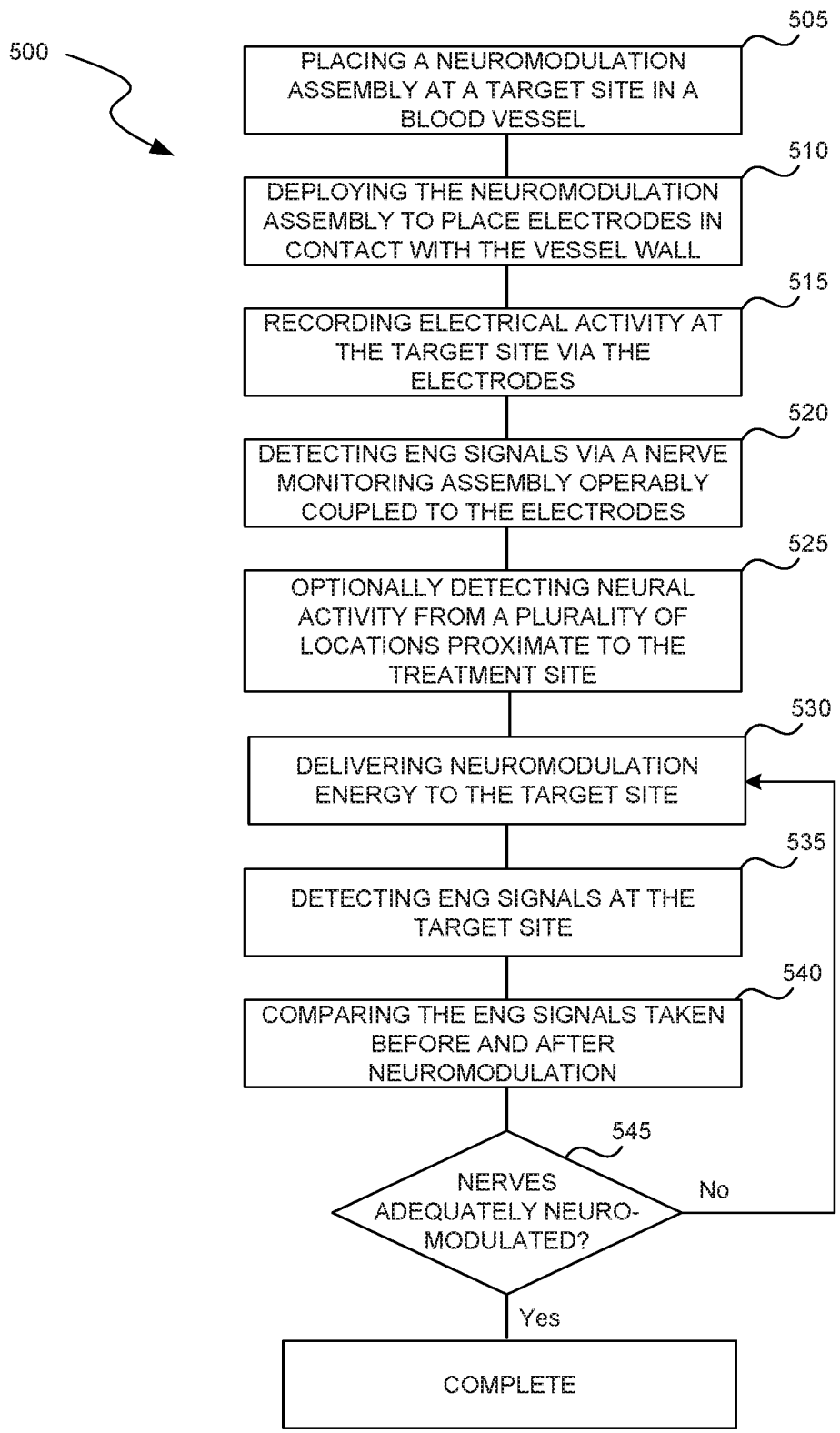
FIG. 5 is a block diagram illustrating a method of monitoring nerve activity in accordance with an embodiment of the present technology.

FIG. 5 is a block diagram illustrating a method 500 of monitoring nerve activity using the system 100 of FIGS. 1-4C or another suitable system in accordance with an embodiment of the present technology. The method 500 can include intravascularly placing a neuromodulation assembly (e.g., the neuromodulation assembly 120 of FIG. 1) at a target site in a blood vessel (block 505), and deploying the neuromodulation assembly from a delivery state (e.g., a low-profile configuration) to a deployed state (e.g., an expanded configuration) to place two or more electrodes, contacts, and/or other energy delivery elements at least substantially in contact with the vessel wall (e.g., as shown in FIG. 3B; block 510).

The method 500 can further include recording electrical activity at the target site via the electrodes (block 515). The recorded electrical activity can then be processed using a nerve monitoring assembly (e.g., the nerve monitoring assembly 128 of FIG. 1) operably coupled to the electrodes to detect ENG signals (block 520). The nerve monitoring assembly can include an amplifier assembly that is electrically coupled to the electrodes in a QT, TT, and/or AT arrangement (e.g., as described above with reference to FIGS. 4A-4C). In various embodiments, neural activity can be detected from several locations at and/or proximate to the target site (e.g., two or more positions along the length of the vessel; block 525), and the ENG signals from the various locations can be averaged to provide a baseline ENG of neural activity before neuromodulation. In other embodiments, neural recordings can be taken from different electrode pairs and compared to provide an understanding of the neural activity along the vessel and/or to select which electrode pair or pairs provide the best ENG signal (e.g., the clearest or strongest ENG signal). If the ENG signal is low or indeterminable, the operator may optionally stimulate neural activity with a short current pulse supplied by one of the electrodes (e.g., a first electrode), and the other electrodes (e.g., a second, third, and/or fourth electrode) can be used to record the resultant neural activity.

After the baseline ENG has been detected, the method 500 can continue by delivering neuromodulation energy to the target site via the electrodes (block 530). In certain embodiments, the same electrodes that are used to detect the neural activity can be used to deliver the neuromodulation energy to the treatment site. In other embodiments, different electrodes can be used for neuromodulation and recording. In further embodiments, neuromodulation energy can be delivered to the target site using other modalities with various different types of energy applicators (e.g., cryotherapeutic applicators, ultrasound transducers, etc.).

The method 500 can further include detecting ENG signals proximate to the treatment site after the neuromodulation energy has been applied (block 535). As discussed above, the ENG signals can be detected by the nerve monitoring assembly using the recordings taken from one or more pairs of electrodes and/or other contacts. The operator can optionally record neural activity from a plurality of different electrode pairs and/or at a plurality of locations proximate to the target site. The various neural recordings can be compared with each other and/or averaged. The post-neuromodulation ENG can then be compared with the ENG taken before neuromodulation (block 540). Decreases (e.g., substantial decreases) in a parameter (e.g., amplitude) of the ENG signals after neuromodulation may indicate sufficient treatment of nerves proximate to the target site. For example, a decrease in amplitude of the ENG signals of 20%, 30%, 40%, 50%, 60%, 70%, 80%, and/or over 90% may indicate sufficient treatment of the target nerves. Using this information, the method 500 can then determine whether the nerves have been adequately modulated (block 545). For example, if the amplitude observed in ENG is below a threshold value, then the neuromodulation step may have effectively modulated or stopped conduction of the adjacent nerves and the neuromodulation process can be considered complete. However, if nerve activity is detected above a threshold value, the process of neuromodulating (block 530) and monitoring the resultant nerve activity (block 535) can be repeated until the nerves have been effectively modulated. The method 500 can optionally be repeated after a time period (e.g., 5-30 minutes, 2 hours, 1 day, etc.) to confirm that the nerves were adequately ablated (e.g., rather than merely being stunned).

The method 500 and the system 100 (FIG. 1) used to implement the method 500 can monitor neural activity and deliver therapeutic energy to modulate nerves to provide real time feedback of the effectiveness of a neuromodulation treatment. Both the recording of neural activity and the delivery of therapeutic energy can be provided by a single device (e.g., the neuromodulation catheter 102 (FIG. 1)), rather than a device dedicated to nerve monitoring and a separate device dedicated to neuromodulation that would each need to be delivered separately to the treatment site. In various embodiments, the same elements (e.g., electrodes) can be used to provide both the recording and energy delivery function. For example, the same signal wires that run along the length of a catheter to the electrodes can be used both to transmit recorded neural signals to the nerve monitoring assembly and deliver energy from the energy generator to the electrodes. In addition, the method 500 can differentiate ENG signals from EMG signals using recordings taken intravascularly positioned electrodes.

Figure 6:
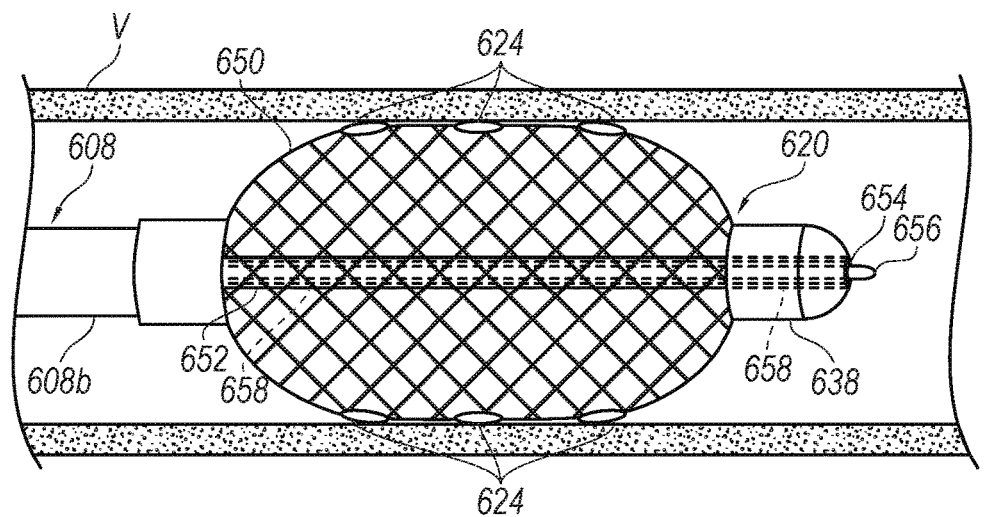
FIG. 6 is a side view of a distal portion of a neuromodulation catheter configured in accordance with another embodiment of the present technology.

FIG. 6 is a side view of a neuromodulation assembly 620 at a distal portion of a neuromodulation catheter configured in accordance with another embodiment of the present technology. The neuromodulation assembly 620 includes various features generally similar to those of the neuromodulation assembly 120 described above with reference to FIGS. 1-3B. For example, the neuromodulation assembly 620 can be attached to a distal portion 608b of a shaft 608 and include a plurality of energy delivery elements 624 (e.g., electrodes) and/or contacts configured to contact a vessel wall V when the neuromodulation assembly 620 is in a deployed state (e.g., shown in FIG. 6).

In the embodiment illustrated in FIG. 6, the energy delivery elements 624 are supported by an expandable mesh structure 650. For example, the energy delivery elements 624 may be proximate to, adjacent to, adhered to, and/or woven into the mesh structure 650. In other embodiments, the energy delivery elements 624 may also be formed by the mesh structure 650 itself (e.g., the fibers of the mesh may be capable of delivering energy). Whether the energy delivery elements 624 are mounted on or integrated into the mesh structure 650, the mesh structure 650 can be expanded such that the energy delivery elements 624 contact with the vessel wall V. Once in contact with the vessel wall V, the energy delivery elements 624 may deliver power independently of each other (i.e., may be used in a monopolar fashion), either simultaneously or progressively, and/or may deliver power between any desired combination of the elements (i.e., may be used in a bipolar fashion). In addition, the energy delivery elements 624 can perform a nerve monitoring function by detecting neural activity before and/or after in energy delivery. In other embodiments, some of the energy delivery elements 624 and/or other contacts on the mesh structure 650 can be configured solely for nerve recording and the other contacts can be configured for energy delivery.

As shown FIG. 6, the neuromodulation assembly 620 can further include a tube 652 or other type of shaft that extends through the length of the mesh structure 650, and a distal member 638 (e.g., a collar, shaft, or cap) at the distal end portion of the mesh structure 650 coupled to the tube 652. The distal member 638 can include a rounded distal portion to provide atraumatic insertion of the neuromodulation assembly 620 into a vessel and an opening 654 that allows the neuromodulation assembly 620 to be threaded over a guide wire 656 for intravascular delivery to a target site. In addition, the shaft 608, the tube 652, the mesh structure 650, and/or the distal member 638 may have a lumen sized and shaped to slideably accommodate a control wire 658. The control wire 658 can facilitate the expansion and/or contraction of the mesh structure 650 when it is pulled or pushed (e.g., at the proximal end of the neuromodulation catheter). For example, pulling (i.e., an increase in tension) of control wire 658 may shorten the mesh structure 650 to increase its diameter placing it in an expanded configuration (e.g., FIG. 6), whereas pushing (i.e., an increase in compression) of control wire 658 may lengthen the mesh structure 650 to a compressed configuration. As shown in FIG. 6, the control wire 658 can be a hollow tube that can be passed over the guide wire 656. In other embodiments, the control wire 658 may be a solid structure (e.g., made from a metal or polymer). Further details and characteristics of neuromodulation assemblies with mesh structures are including in International Patent Application No. PCT/US2011/057153 (International Patent Application Publication No. WO2012/054862), which is herein incorporated by reference in its entirety.

Figure 7:
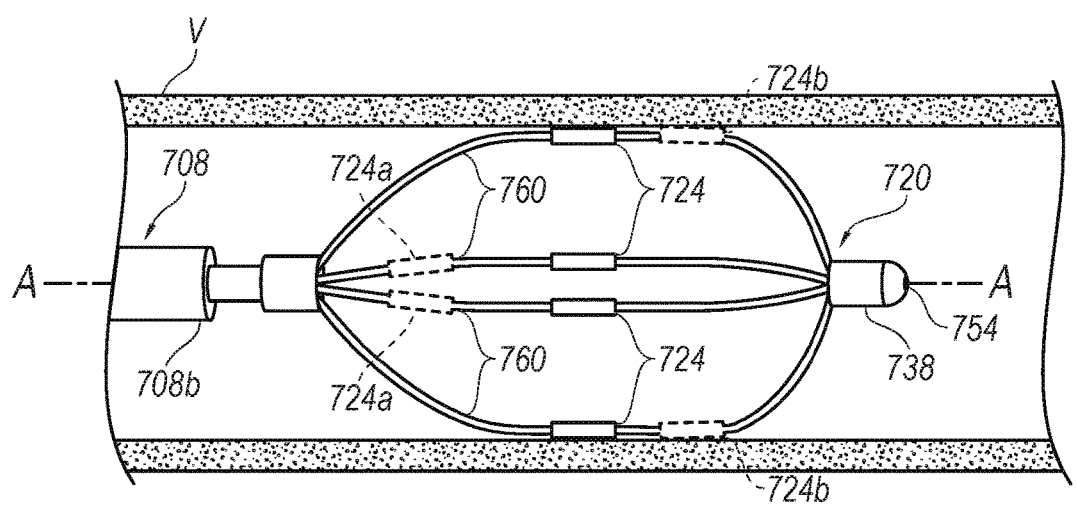
FIG. 7 is a side view of a distal portion of a neuromodulation catheter configured in accordance with yet another embodiment of the present technology.

FIG. 7 is a side view of a neuromodulation assembly 720 at a distal portion of a neuromodulation catheter configured in accordance with yet another embodiment of the present technology. The neuromodulation assembly 720 includes various features generally similar to those of the neuromodulation assemblies 120 and 620 described above. For example, the neuromodulation assembly 720 can be attached to a distal portion 708b of a shaft 708 and include a plurality of contacts or energy delivery elements 724 configured to be placed into contact with a vessel wall V when the neuromodulation assembly 720 is deployed within a vessel (e.g., FIG. 7). An atraumatic (e.g., rounded) distal member 738 can be attached to the distal portion of the neuromodulation assembly 720 and can include a distal guide wire opening 754 to facilitate intravascular delivery of the neuromodulation assembly 720 to a target site.

In the embodiment illustrated in FIG. 7, the neuromodulation assembly 720 further includes a plurality of supports 760 that define an expandable basket structure and carry the energy delivery elements 724. The proximal ends of the supports 720 can be attached or otherwise connected to the distal portion 708b of the shaft 708, and the distal ends of the supports 760 can be attached or otherwise connected to the distal member 738. At least one of the distal portion 708b of the shaft 708 and the distal member 738 can be moveable along the longitudinal dimension A-A of the shaft 708 to transform the neuromodulation assembly 720 from a low-profile delivery state to an expanded deployed state in which the energy delivery elements 724 contact in the inner wall V of at a target site.

As shown in FIG. 7, the energy delivery elements 724 can be spaced angularly apart from each other around the longitudinal dimension A-A of the shaft 708 at a common area along the length of the longitudinal dimension A-A. This arrangement places the energy delivery elements 724 in contact with the vessel wall V to provide an at least substantially circumferential exposure (e.g., for neural recording and/or neuromodulation) in a common plane perpendicular to the longitudinal dimension A-A of the shaft 708. In other embodiments, the energy delivery elements 724 can have other suitable configurations. For example, one or more energy delivery elements 724 can be spaced along the length of the supports 760 to provide nerve monitoring and/or neuromodulation at different zones along the length of the vessel and/or the neuromodulation assembly 720 can include a different number of supports 760 than the four supports 760 illustrated in FIG. 7 (e.g., to provide nerves with more fully circumferential exposure the energy delivery elements 724). In further embodiments, the energy delivery elements 724 can be positioned in a staggered relationship relative to each other along the length of the neuromodulation assembly 720. For example, first electrodes 724a (shown in broken lines) at a proximal portion of two of the supports 760 can be longitudinally offset from second energy delivery elements 724b (shown in broken lines) on distal portions of two other longitudinal supports 760. The first electrodes 724a can also be angularly offset from the second electrodes 724b by, for example, 90° or some other suitable angle.

The energy delivery elements 724 can be electrodes configured to provide both energy delivery (e.g., RF energy) and recording of electrical activity at the target site. In other embodiments, some of the energy delivery elements 724 can serve solely as contacts for detecting neural signals while others are configured for energy delivery. In further embodiments, at least some of the energy delivery elements 724 can be configured to provide a form of energy other than electrical current (e.g., RF energy) to the target site, while others can provide the nerve monitoring function. For example, at least some of the energy delivery elements 724 can be defined by radiation emitters that expose target nerves to radiation at a wavelength that causes a previously administered photosensitizer to react, such that it damages or disrupts the nerves. The radiation emitters can be optical elements coupled to fiber optic cables (e.g., extending through the shaft 708) for delivering radiation from a radiation source (e.g., an energy generator) at an extracorporeal location to the target tissue at the vessel, or may be internal radiation sources (e.g., LEDs) that are electrically coupled to a power source at an extracorporeal location via electrical leads within the shaft 708.

In embodiments where one or more of the energy delivery elements 724 are defined by radiation emitters, a photosensitizer (e.g., oxytetracycline, a suitable tetracycline analog, and/or other suitable photosensitive compounds that preferentially bind to neural tissue) can be administered to a patient (e.g., orally, via injection, through an intravascular device, etc.), and preferentially accumulate at selected nerves (e.g., rather than other tissues proximate to the selected nerves). For example, more of the photosensitizer can accumulate in perivascular nerves around a blood vessel than in the non-neural tissues of the blood vessel. The mechanisms for preferentially accumulating the photosensitizer at the nerves can include faster uptake by the nerves, longer residual times at the nerves, or a combination of both. After a desired dosage of the photosensitizer has accumulated at the nerves, the photosensitizer can be irradiated using energy delivery elements 724. The energy delivery elements 724 can deliver radiation to the target nerves at a wavelength that causes the photosensitizer to react such that it damages or disrupts the nerves. For example, the photosensitizer can become toxic upon exposure to the radiation. Because the photosensitizer preferentially accumulates at the nerves and not the other tissue proximate the nerves, the toxicity and corresponding damage is localized primarily at the nerves. This form of irradiative neuromodulation can also or alternatively be incorporated in any one of the neuromodulation assemblies described herein. Further details and characteristics of neuromodulation assemblies with radiation emitters are included in U.S. patent application Ser. No. 13/826,604, which is incorporated herein by reference in its entirety.

Figure 8:
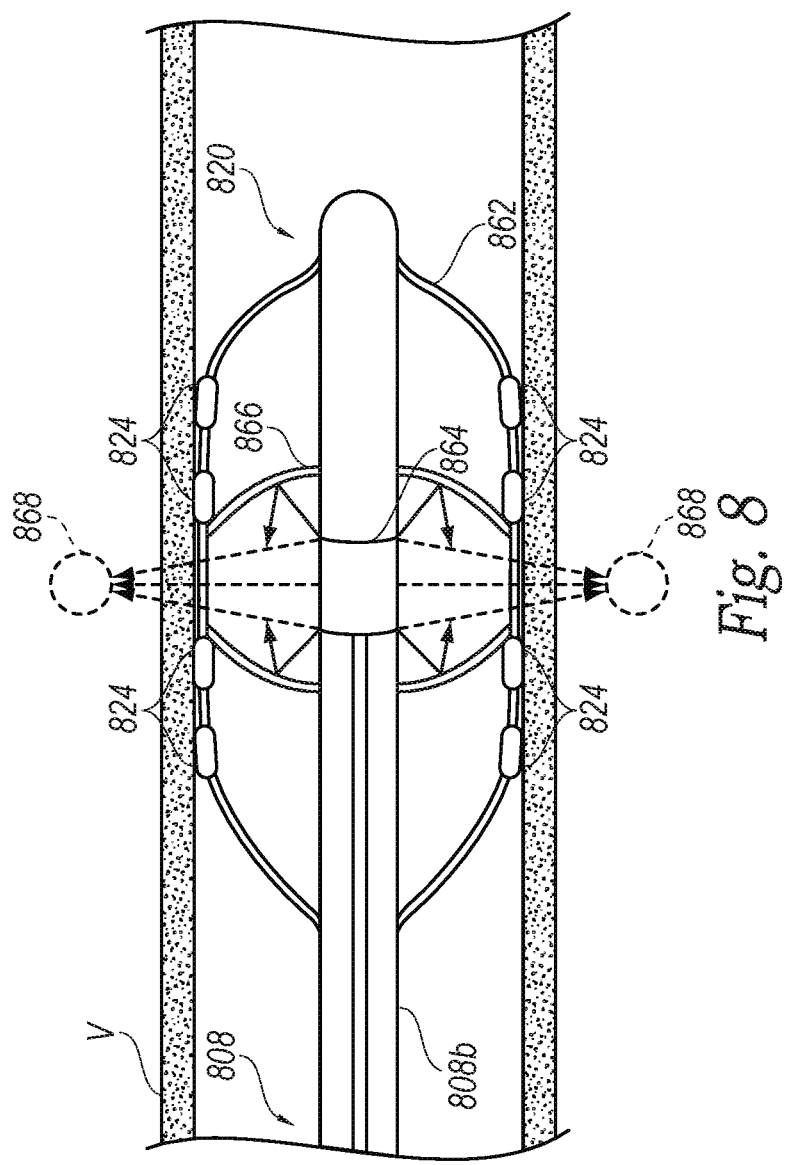
FIG. 8 is a side view of a distal portion of a neuromodulation catheter configured in accordance with a further embodiment of the present technology.

FIG. 8 is a side view of a neuromodulation assembly 820 at a distal portion of a neuromodulation catheter configured in accordance with a further embodiment of the present technology. The neuromodulation assembly 820 includes various features generally similar to the features of the neuromodulation assemblies 120, 620 and 720 described above. For example, the neuromodulation assembly 820 can be attached to a distal portion 808*b* of a shaft 808 and include a plurality of energy delivery elements or contacts 824 configured to be placed into contact with a vessel wall V when the neuromodulation assembly 820 is deployed within a vessel (e.g., FIG. 8). In the embodiment illustrated in FIG. 8, the contacts 824 are carried by an outer expandable body 862 (e.g., a balloon) that positions the contacts 824 against a vessel wall V when the expandable body 862 is deployed (e.g., inflated or otherwise expanded) within the vessel. The shaft 808 and/or another suitable elongated member connected to the shaft 808 can extend at least partially through the expandable body 862 and carry an ultrasound transducer 864. The ultrasound transducer 864 may be configured to provide therapeutically effective energy (e.g., HIFU) and, optionally, provide imaging information that may facilitate placement of the transducer 864 relative to a blood vessel, optimize energy delivery, and/or provide tissue feedback (e.g. to determine when treatment is complete). Further, depending on the particular arrangement of the ultrasound transducer 864, the lesion created by the application of ultrasound energy may be limited to very specific areas (e.g., focal zones or focal points) on the periphery of the vessel wall V or on the nerves themselves. For example, it is expected that the average ultrasound intensity for neural modulation (e.g., ablation of renal nerves) may be in the range of about 1-4 kW/cm$^2$ and may be delivered for a total of 10-60 seconds to create one focal lesion.

In the embodiment illustrated in FIG. 8, the neuromodulation assembly 820 further includes an inner expandable body 866 (e.g., a balloon) positioned within the outer expandable body 862 and around the ultrasound transducer 864. The inner expandable body 866 can be filled with a sound-conducting medium (e.g. water, a conductive medium, etc.) and act as an acoustic lens and transmission media for the emitted ultrasonic energy. As indicated by the arrows, the waves emitted by the ultrasound transducer 864 can be formed into one or more focal beams focusing on corresponding focal points or regions 868 (e.g., about 0-5 mm deep in the surrounding tissue). In other embodiments, other features (e.g., an acoustically reflective material) can be used to form the waves into one or more focal beams.

As shown in FIG. 8, the outer expandable body 862 may be configured to position the contacts 824 away from the waves emitted by the ultrasound transducer 864 to avoid undesirably heating the contacts 824. Optionally, the outer expandable body 862 can be filled with a gas to contain the energy emitted by the ultrasound transducer 864 and inhibit it from escaping in the undesired directions. This form of ultrasound-based neuromodulation can also or alternatively be incorporated in any one of the neuromodulation assemblies described above or below. Additional features and alternative embodiments of ultrasound-induced neuromodulation devices are disclosed in U.S. patent application Ser. No. 12/940,0922 (U.S. Patent Publication No. 2011/0112400), which is incorporated herein by reference in its entirety.

Figure 9:
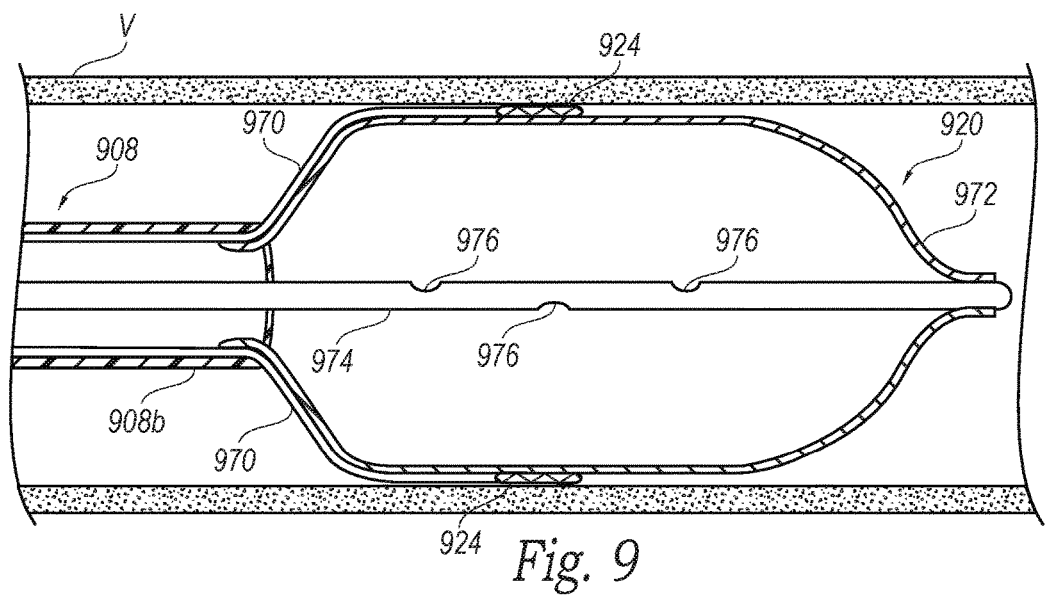
FIG. 9 is a partial cross-sectional side view of a distal portion of a neuromodulation catheter configured in accordance with yet another embodiment of the present technology.

FIG. 9 is a partial cross-sectional side view of a neuromodulation assembly 920 at a distal portion of a neuromodulation catheter configured in accordance with yet another embodiment of the present technology. The neuromodulation assembly 920 includes various features generally similar to the features of the neuromodulation assemblies 120, 620, 720 and 820 described above. For example, the neuromodulation assembly 920 can be attached to a distal portion 908*b* of a shaft 908 and include a plurality of energy delivery elements or contacts 924 configured to be placed into contact with a vessel wall V when the neuromodulation assembly 920 is deployed within a vessel (e.g., FIG. 9). As shown in FIG. 9, the energy delivery elements 924 can be electrically coupled to corresponding conductive leads 970 (e.g., electrical wires) that extend through or along the shaft 908. The leads 970 can operably couple the energy delivery elements 924 to an energy source (e.g., the energy generator 126 of FIG. 1) and/or a nerve monitoring assembly (e.g., the nerve monitoring assembly 128 of FIG. 1) at a proximal portion of the shaft 908.

As shown in FIG. 9, the neuromodulation assembly 920 can further include a cryogenic applicator 972 (e.g., a balloon or other expandable member) that can expand radially outward to press or otherwise contact the inner surface of the vessel wall V. For example, the cryogenic applicator 972 can define at least a portion of an expansion chamber in which a refrigerant expands or otherwise flows to provide cryogenic cooling. A supply lumen 974 can be fluidly coupled to a refrigerant source (e.g., a refrigerant cartridge or canister; not shown) at its proximal end portion, and may be sized to retain at least a portion of the refrigerant that reaches the expansion chamber at a high pressure liquid state. The supply lumen 974 can include one or more orifices or openings 976 from which refrigerant can expand into the expansion chamber, or refrigerant can be configured to expand from a distal opening of a capillary tube (not shown) extending from the supply lumen 974. In various embodiments, the openings 976 may have a cross-sectional area less than that of the supply lumen 974 to impede the flow of refrigerant proximate the expansion chamber, thereby increasing the pressure drop of the refrigerant entering the expansion chamber and concentrating the refrigeration power at the cryogenic applicator 974. For example, the openings 976 can be sized relative to the area and/or length of an exhaust lumen (e.g., defined by a distal portion of the shaft 908) to provide a sufficient flow rate of refrigerant, produce a sufficient pressure drop when the refrigerant enters the expansion chamber, and allow for sufficient venting of expanded refrigerant through the shaft 908 to establish and maintain cooling at the cryogenic applicator 972.

In operation, a liquid refrigerant can expand into a gaseous phase as it passes through the openings 976 of the supply lumen 974 into the expansion chamber (defined by at least a portion of the cryogenic applicator 974), thereby inflating the cryogenic applicator 972. The expansion of the refrigerant causes a temperature drop in the expansion chamber, thereby forming one or more cooling zones around at least a portion of the cryogenic applicator 972. In various embodiments, the cooling zones created by the cryogenic applicator 972 can provide therapeutically effective cooling to nerves proximate to the vessel wall V, while the contacts 924 serve a nerve monitoring function. In other embodiments, the cryogenic applicator 972 can be provided by a non-expandable member, such a cryoprobe at the distal portion 908*b* of the shaft 908 (e.g., a FREEZOR catheter available from Medtronic, Inc. of Minneapolis, Minn.).

In further embodiments, the contacts 924 can be configured to provide resistive heating in and/or at the tissue to raise the temperatures at hyperthermic zones in the vessel wall V and the surrounding neural fibers to provide therapeutically-effective neuromodulation, and the cryogenic applicator 972 can be configured to form non-therapeutic cooling zones before, during, and/or after the delivery of hyperthermic energy by the contacts 924. For example, concurrently with the application of hyperthermic energy via the contacts 924, the cooling zone can be provided at a relatively low refrigeration power, e.g., a power less than that required to induce neuromodulation. The cooling zone can cool the contacts 924 and/or the body tissue at or proximate to the target site (e.g., the inner surface of vessel wall V). The cooling zone provided by the cryogenic applicator 972 is expected to maintain lower temperatures, and thereby reduce thermal trauma in the tissue proximate the inner surface of the vessel wall V during hyperthermic neuromodulation. The hyperthermic zone may also extend or focus more on the exterior area of the vessel wall V where the nerves reside. Therefore, the neuromodulation assembly 920 can provide a reverse thermal gradient across a portion of the vessel wall V to provide hyperthermic neuromodulation at a depth in the tissue, while reducing potential hyperthermal effects on the vessel tissue closer to the neuromodulation assembly 920.

The cryotherapeutic neuromodulation and/or cryogenic cooling described above can also or alternatively be incorporated in any one of the neuromodulation assemblies described above. Further details and characteristics of neuromodulation assemblies with cryogenic applicators are included in International Patent Application No. PCT/US2011/057514 and U.S. patent application Ser. No. 13/458,859, each of which is incorporated herein by reference in its entirety.

Figure 10:
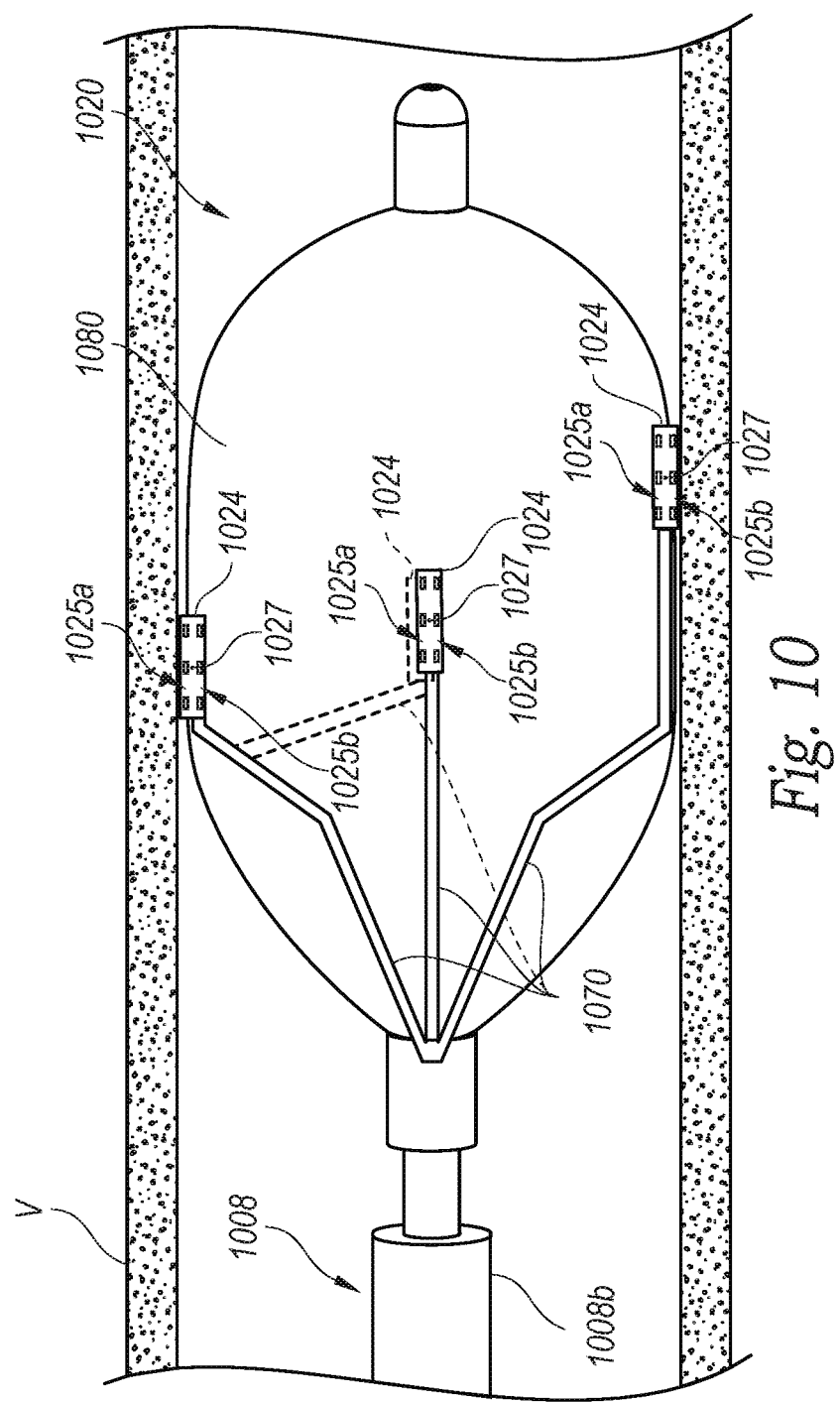
FIG. 10 is a side view of a distal portion of a neuromodulation catheter configured in accordance with still another embodiment of the present technology.

FIG. 10 is a side view of a neuromodulation assembly 1020 at a distal portion of a neuromodulation catheter configured in accordance with yet another embodiment of the present technology. The neuromodulation assembly 1020 includes various features generally similar to the features of the neuromodulation assemblies 120, 620, 720, 820 and 920 described above. For example, the neuromodulation assembly 1020 can be attached to a distal portion 1008*b* of a shaft 1008 and include a plurality of energy delivery elements or contacts 1024 configured to be placed into contact proximate to a vessel wall V when the neuromodulation assembly 1020 is deployed within a vessel. Each energy delivery element 1024 can be a bipolar element having one or more oppositely biased contact pairs. For example, the energy delivery elements 1024 can each have a row of positive contacts 1025*a* and a row of negative contacts 1025*b*. In operation, a small electrical field is established between the positive contacts 1025*a* and the negative contacts 1025*b*. Each energy delivery element 1024 can also include a thermistor 1026. The energy delivery elements 1024 with the various contacts 1025*a-b* and thermistors 1026 can be flex circuits attached to the balloon 1080 or printed directly onto the balloon 1080.

As shown in FIG. 10, the neuromodulation assembly 1020 can further include a balloon 1080 or other expandable member that carries the energy delivery elements 1024 (e.g., electrodes). The balloon 1080 can be inflated with a fluid to place the energy delivery elements 1024 in contact with the vessel wall V and, optionally, occlude the vessel. For example, the balloon 1080 can be inflated by injecting a gas into the balloon 1080 via an inflation lumen (not shown) that extends along the length of the shaft 1008. In other embodiments, a fluid (e.g., a gas, a cryogenic fluid) can be circulated through the balloon 1080 to inflate the device.

As further shown in FIG. 10, the plurality of energy delivery elements 1024 can be electrically coupled to a corresponding plurality of leads 1070 that are coupled to or positioned about the expandable member 1080. In various embodiments, the leads 1070 can be part of a flex circuit that easily expands or collapses with the expandable member 1080. The leads 1070 can be electrically coupled to an energy source (e.g., the energy generator 126 of FIG. 1) and/or a nerve monitoring assembly (e.g., the nerve monitoring assembly 128 of FIG. 1) at a proximal portion of the shaft 1008 by wires that extend through or along the shaft 1008 or via a wireless connection. Accordingly, the energy delivery elements 1024 can provide both a nerve recording function and a neuromodulation function.

In the embodiment illustrated in FIG. 10, the energy delivery elements 1024 are defined by individual bipolar point electrodes that are spaced at multiple lengthwise and angular positions relative to the outer surface of the balloon 1080 and the vessel wall V. For example, the four energy delivery elements 1024 shown in FIG. 10 can be angularly offset from each other by about 90°. In other embodiments, the energy delivery elements 1024 can be angularly offset from each other by different degrees (e.g., 60°, 80°, 180°, etc.) depending on the number of energy delivery elements 1024 and/or their relative spacing along the length of the balloon 1080. The lengthwise and/or angularly offset energy delivery elements 1024 can provide non-continuous circumferential neuromodulation and/or neural recording without having to reposition the neuromodulation assembly 1020. The illustrated embodiment shows four energy delivery elements 1024, but other embodiments can include different numbers of energy delivery elements (e.g., 1-12 energy delivery elements 1024). In further embodiments, the energy delivery elements 1024 can have other suitable configurations on the outer surface of the balloon 1080, and/or the energy delivery elements 1024 may have other suitable structures. For example, in certain embodiments one or more of the energy delivery elements 1024 can be defined by circular electrodes and/or spiral-shaped electrodes that extend around the outer surface of the balloon 1080. Such configurations can provide partial or full circumferential neuromodulation and/or neural recording along the vessel wall V.

III. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a target site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

III. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 11:
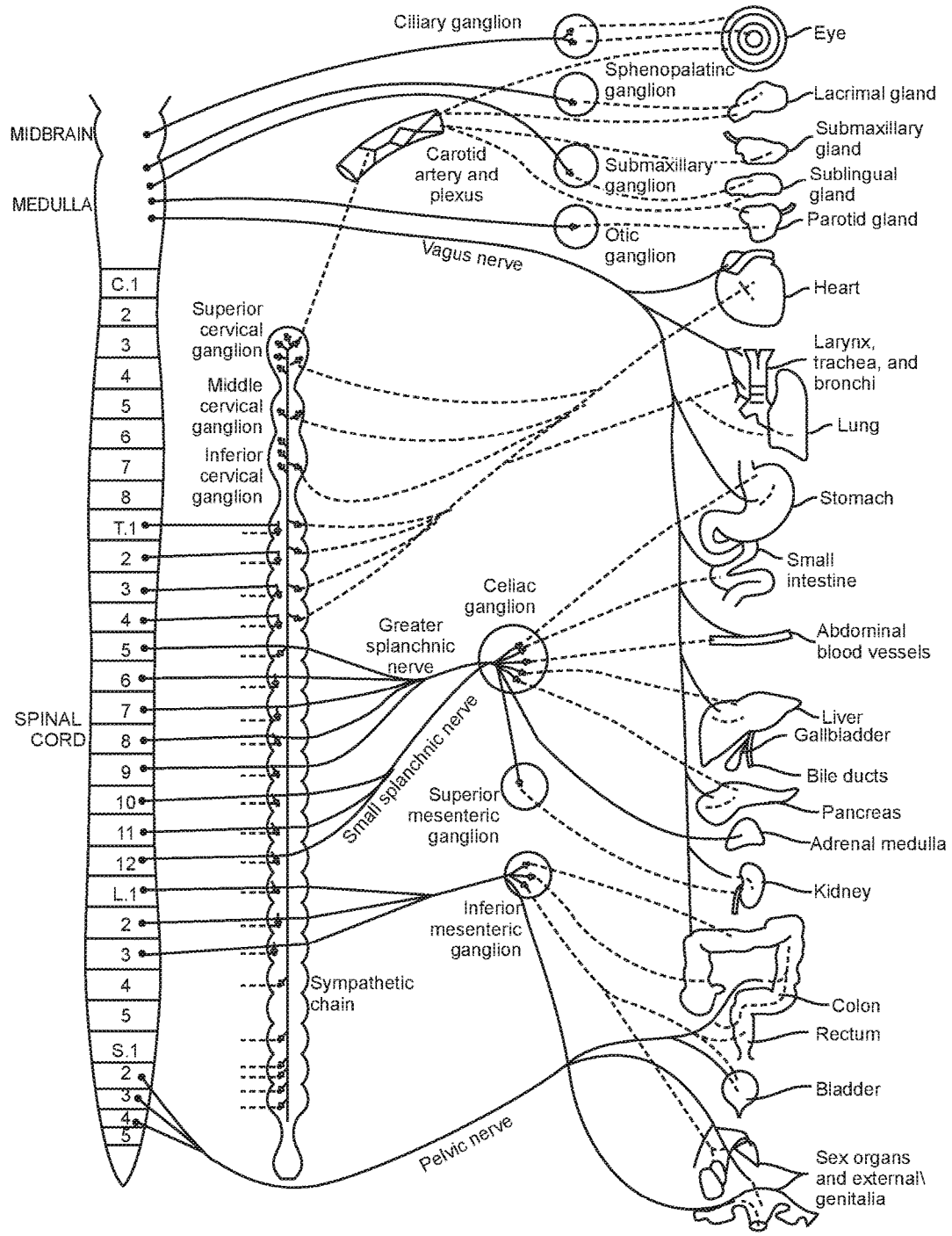
FIG. 11 is a conceptual illustration of the sympathetic nervous system (SNS) and how the brain communicates with the body via the SNS.

As shown in FIG. 11, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 12:
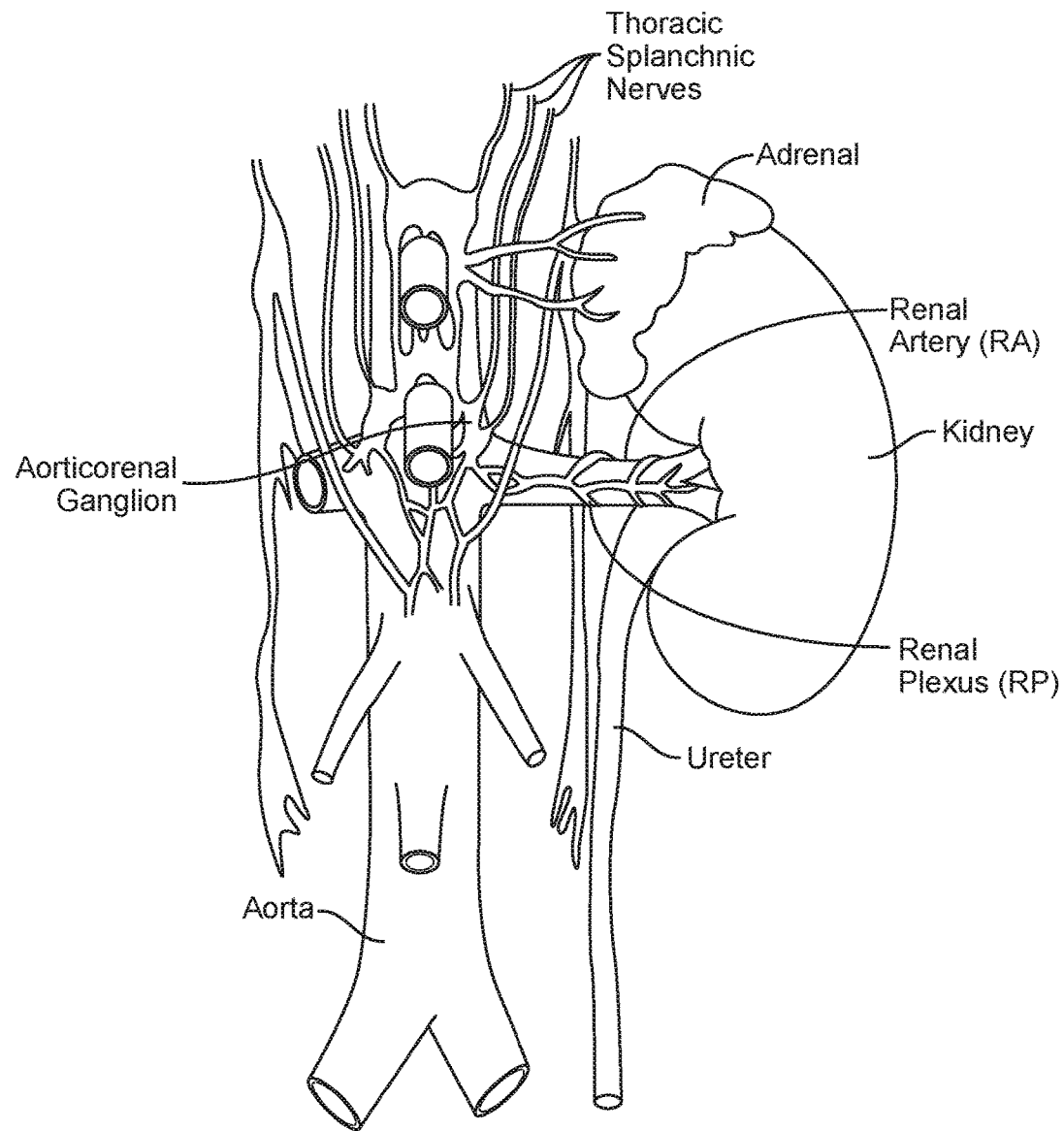
FIG. 12 is an enlarged anatomic view of nerves innervating a left kidney to form the renal plexus surrounding the left renal artery.

As FIG. 12 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 13A:
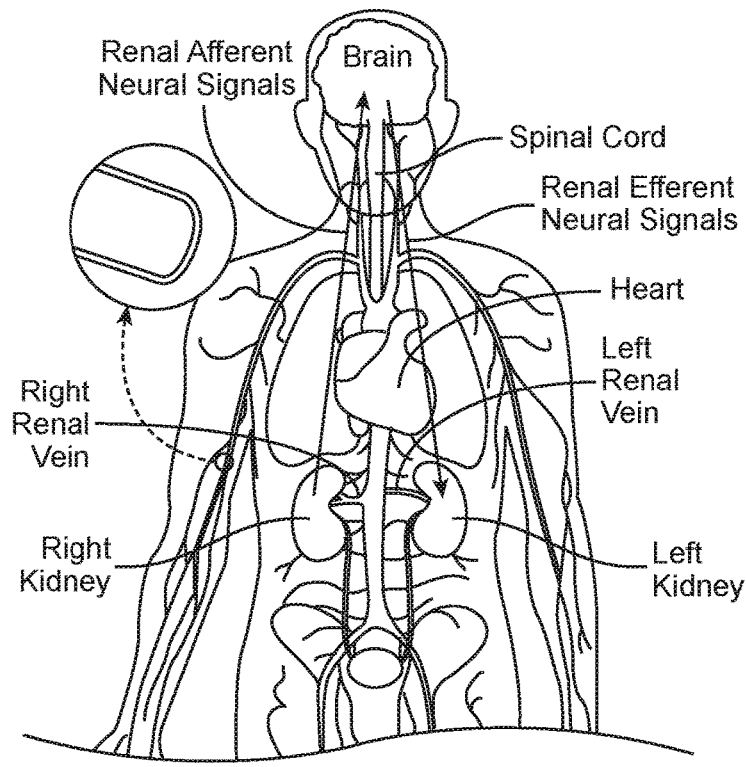
FIGS. 13A and 13B are anatomic and conceptual views, respectively, of a human body depicting neural efferent and afferent communication between the brain and kidneys.
Figure 13B:
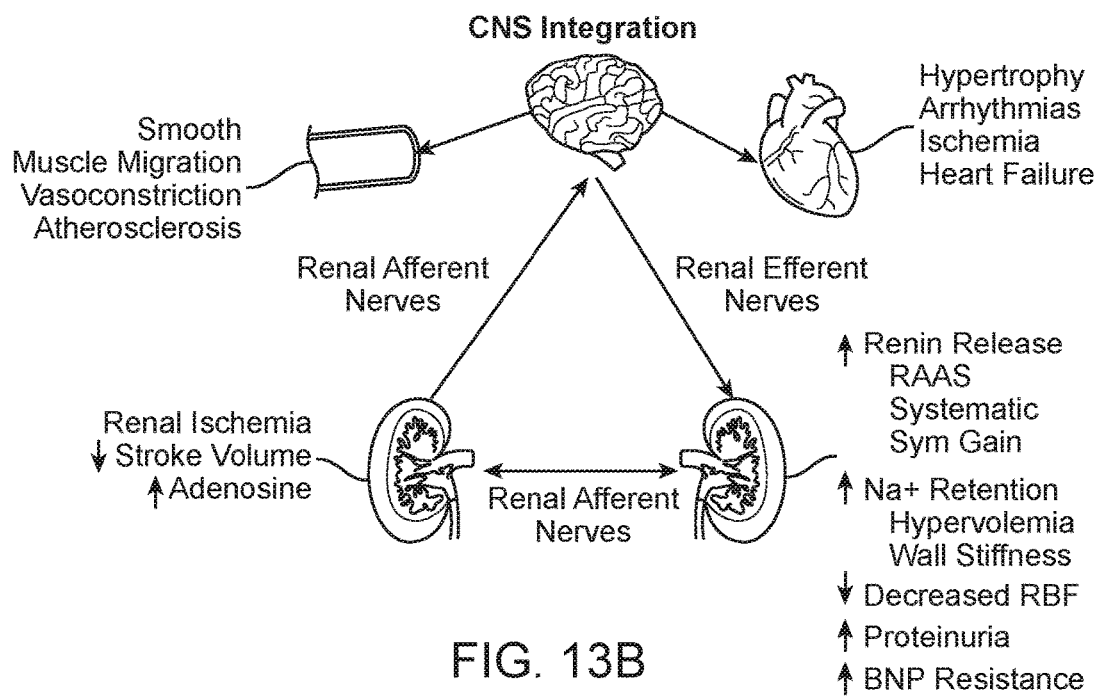

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 13A and 13B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 11. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 14A:
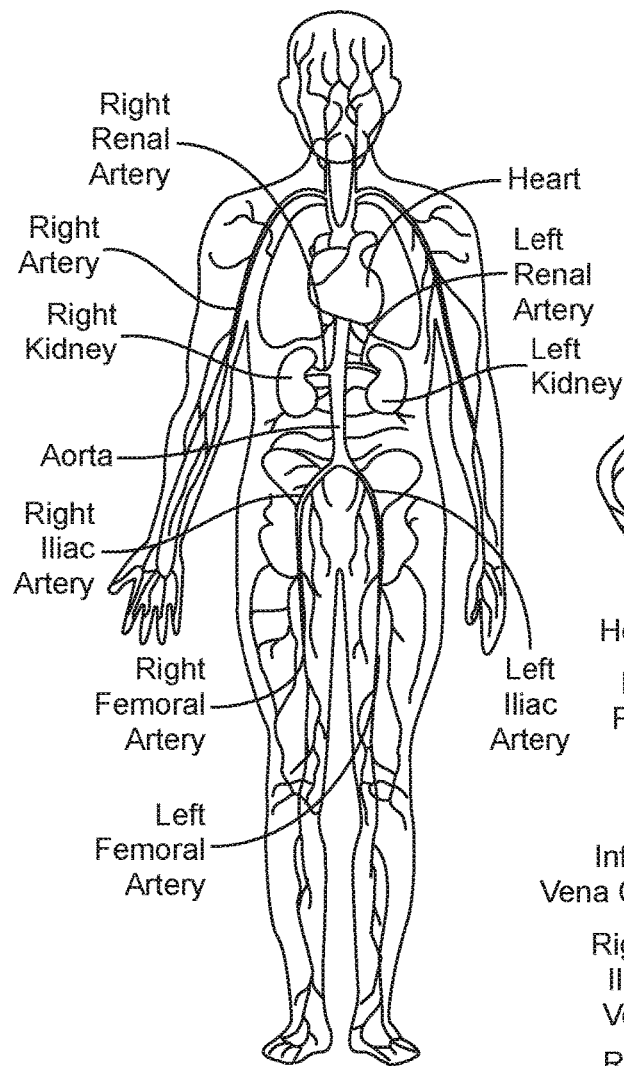
FIGS. 14A and 14B are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 14A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 14B:
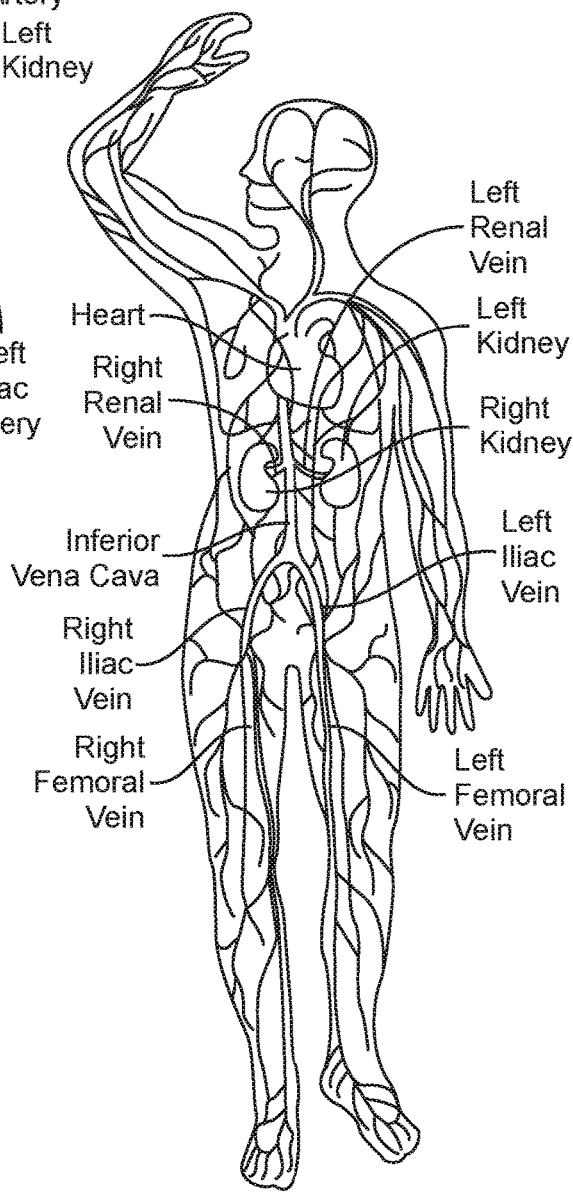

As FIG. 14B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

IV. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. A neuromodulation catheter, comprising:
   an elongated shaft having a distal portion and a proximal portion, wherein the distal portion of the shaft is configured for intravascular delivery to a target site within a blood vessel of a human patient;
   an array of electrodes at the distal portion of the shaft, wherein the electrodes are configured to record electroneurogram (ENG) signals proximate to the target site from within the blood vessel, and wherein the electrodes are further configured to deliver energy to the target site to ablate nerves proximate to the target site; and
   a connector operably coupled to the electrodes, wherein the connector is at the proximal portion of the shaft and configured to electrically couple the electrodes to an energy generator and to a nerve monitoring assembly configured to remain external to the patient, and
   wherein the nerve monitoring assembly is operably coupled to the electrodes via signal wires extending through the connector and the elongated shaft, and
   wherein the nerve monitoring assembly is configured to differentiate the ENG signals from electromyogram (EMG) signals.

2. The neuromodulation catheter of claim 1 wherein the distal portion of the shaft comprises a support member having a spiral shape and configured to contact an interior wall of the blood vessel when the support member is in a deployed state, and wherein the electrodes are spaced apart from each other along a length of the support member.

3. The neuromodulation catheter of claim 2 wherein the array of electrodes comprises four electrodes spaced apart from each other along the length of the support member.

4. The neuromodulation catheter of claim 1 wherein the elongated shaft is configured for intravascular delivery to a renal blood vessel of the patient.

5. The neuromodulation catheter of claim 1 wherein the elongated shaft is configured for intravascular delivery to a renal artery of the patient.

6. The neuromodulation catheter of claim 1 wherein the generator and the nerve monitoring assembly are integrated with each other in a console.

* * * * *